US012599787B2

(12) United States Patent
Xu et al.

(10) Patent No.: US 12,599,787 B2
(45) Date of Patent: Apr. 14, 2026

(54) ALL-IN-ONE ULTRASOUND SYSTEMS AND METHODS INCLUDING HISTOTRIPSY

(71) Applicant: THE REGENTS OF THE UNIVERSITY OF MICHIGAN, Ann Arbor, MI (US)

(72) Inventors: Zhen Xu, Ann Arbor, MI (US); Jonathan Robert Sukovich, Ann Arbor, MI (US); Timothy Lewis Hall, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 18/568,045

(22) PCT Filed: Apr. 7, 2022

(86) PCT No.: PCT/US2022/023786
§ 371 (c)(1),
(2) Date: Dec. 7, 2023

(87) PCT Pub. No.: WO2022/260747
PCT Pub. Date: Dec. 15, 2022

(65) Prior Publication Data
US 2024/0269491 A1 Aug. 15, 2024

Related U.S. Application Data

(60) Provisional application No. 63/197,919, filed on Jun. 7, 2021.

(51) Int. Cl.
*A61N 7/02* (2006.01)
*A61N 7/00* (2006.01)
(52) U.S. Cl.
CPC ........ *A61N 7/02* (2013.01); *A61N 2007/0026* (2013.01); *A61N 2007/0039* (2013.01)

(58) Field of Classification Search
CPC .............. A61N 7/02; A61N 2007/0026; A61N 2007/0039
See application file for complete search history.

(56) References Cited

U.S. PATENT DOCUMENTS

| | | | |
|---|---|---|---|
| 3,243,497 A | 3/1966 | Kendall et al. | |
| 3,679,021 A | 7/1972 | Goldberg et al. | |

(Continued)

FOREIGN PATENT DOCUMENTS

| | | |
|---|---|---|
| AU | 2017222925 B2 | 11/2021 |
| AU | 2023231624 | 9/2024 |

(Continued)

OTHER PUBLICATIONS

Bader et al.; For whom the bubble grows: physical principles of bubble nucleation and dynamics in histotripsy ultrasound therapy; Ultrasound in medicine & biology; 45(5); pp. 1056-1080; May 1, 2019.

(Continued)

*Primary Examiner* — Dixomara Vargas
(74) *Attorney, Agent, or Firm* — Shay Glenn LLP

(57) ABSTRACT

An all-in-one ultrasound therapy system configured for the treatment of tissue is provided, which may include any number of features. Provided herein are systems and methods that provide efficacious non-invasive and minimally invasive therapeutic, diagnostic and research procedures. In particular, provided herein are optimized systems and methods that provide targeted, efficacious ultrasound therapy in a variety of different regions and under a variety of different conditions without causing undesired tissue damage to intervening/non-target tissues or structures. The ultrasound therapy can include modalities such as histotripsy, hyper- (Continued)

thermia/radio-sensitization, HIFU microbubble-enhanced drug delivery, immunotherapy, sonodynamic therapy, and/or neuromodulation.

19 Claims, 6 Drawing Sheets

(56)                    References Cited

U.S. PATENT DOCUMENTS

| | | | |
|---|---|---|---|
| 3,693,415 | A | 9/1972 | Whittington |
| 3,879,699 | A | 4/1975 | Pepper |
| 4,016,749 | A | 4/1977 | Wachter |
| 4,024,501 | A | 5/1977 | Herring et al. |
| 4,051,394 | A | 9/1977 | Tieden |
| 4,114,457 | A | 9/1978 | Thun |
| 4,117,446 | A | 9/1978 | Alais |
| 4,266,747 | A | 5/1981 | Souder, Jr. et al. |
| 4,269,174 | A | 5/1981 | Adair |
| 4,277,367 | A | 7/1981 | Madsen et al. |
| 4,351,038 | A | 9/1982 | Alais |
| 4,406,153 | A | 9/1983 | Ophir et al. |
| 4,440,025 | A | 4/1984 | Hayakawa et al. |
| 4,447,031 | A | 5/1984 | Souder, Jr. et al. |
| 4,453,408 | A | 6/1984 | Clayman |
| 4,483,343 | A | 11/1984 | Beyer et al. |
| 4,483,345 | A | 11/1984 | Miwa |
| 4,548,374 | A | 10/1985 | Thompson et al. |
| 4,549,533 | A | 10/1985 | Cain et al. |
| 4,550,606 | A | 11/1985 | Drost |
| 4,551,794 | A | 11/1985 | Sandell |
| 4,575,330 | A | 3/1986 | Hull |
| 4,622,972 | A | 11/1986 | Giebeler, Jr. |
| 4,625,731 | A | 12/1986 | Quedens et al. |
| 4,641,378 | A | 2/1987 | McConnell et al. |
| 4,669,483 | A | 6/1987 | Hepp et al. |
| 4,689,986 | A | 9/1987 | Carson et al. |
| 4,757,820 | A | 7/1988 | Itoh |
| 4,791,915 | A | 12/1988 | Barsotti et al. |
| 4,819,621 | A | 4/1989 | Ueberle et al. |
| 4,829,491 | A | 5/1989 | Saugeon et al. |
| 4,856,107 | A | 8/1989 | Dory |
| 4,865,042 | A | 9/1989 | Umemura et al. |
| 4,888,746 | A | 12/1989 | Wurster et al. |
| 4,890,267 | A | 12/1989 | Rudolph |
| 4,922,917 | A | 5/1990 | Dory |
| 4,928,672 | A | 5/1990 | Grasser et al. |
| 4,938,217 | A | 7/1990 | Lele |
| 4,957,099 | A | 9/1990 | Hassler |
| 4,973,980 | A | 11/1990 | Howkins et al. |
| 4,984,575 | A | 1/1991 | Uchiyama et al. |
| 4,991,151 | A | 2/1991 | Dory |
| 4,995,012 | A | 2/1991 | Dory |
| RE33,590 | E | 5/1991 | Dory |
| 5,014,686 | A | 5/1991 | Schafer |
| 5,065,751 | A | 11/1991 | Wolf |
| 5,078,140 | A | 1/1992 | Kwoh |
| 5,080,101 | A | 1/1992 | Dory |
| 5,080,102 | A | 1/1992 | Dory |
| 5,091,893 | A | 2/1992 | Smith et al. |
| 5,092,336 | A | 3/1992 | Fink |
| 5,097,709 | A | 3/1992 | Masuzawa et al. |
| 5,111,822 | A | 5/1992 | Dory |
| 5,143,073 | A | 9/1992 | Dory |
| 5,143,074 | A | 9/1992 | Dory |
| 5,150,711 | A | 9/1992 | Dory |
| 5,158,070 | A | 10/1992 | Dory |
| 5,158,071 | A | 10/1992 | Umemura et al. |
| 5,163,421 | A | 11/1992 | Bernstein et al. |
| 5,165,412 | A | 11/1992 | Okazaki |
| 5,174,294 | A | 12/1992 | Saito et al. |
| 5,195,509 | A | 3/1993 | Rentschler et al. |
| 5,209,221 | A | 5/1993 | Riedlinger |
| 5,215,680 | A | 6/1993 | D'Arrigo |
| 5,219,401 | A | 6/1993 | Cathignol et al. |
| 5,222,806 | A | 6/1993 | Roberts |
| 5,230,340 | A | 7/1993 | Rhyne |
| 5,295,484 | A | 3/1994 | Marcus et al. |
| 5,316,000 | A | 5/1994 | Chapelon et al. |
| 5,354,258 | A | 10/1994 | Dory |
| 5,380,411 | A | 1/1995 | Schlief |
| 5,393,296 | A | 2/1995 | Rattner |
| 5,409,002 | A | 4/1995 | Pell |
| 5,431,621 | A | 7/1995 | Dory |
| 5,435,311 | A | 7/1995 | Umemura et al. |
| 5,443,069 | A | 8/1995 | Schaetzle |
| 5,450,305 | A | 9/1995 | Boys et al. |
| 5,469,852 | A | 11/1995 | Nakamura et al. |
| 5,474,071 | A | 12/1995 | Chapelon et al. |
| 5,474,531 | A | 12/1995 | Carter |
| 5,490,051 | A | 2/1996 | Messana |
| 5,492,126 | A | 2/1996 | Hennige et al. |
| 5,501,655 | A | 3/1996 | Rolt et al. |
| 5,520,188 | A | 5/1996 | Hennige et al. |
| 5,523,058 | A | 6/1996 | Umemura et al. |
| 5,524,620 | A | 6/1996 | Rosenschein |
| 5,540,909 | A | 7/1996 | Schutt |
| 5,542,935 | A | 8/1996 | Unger et al. |
| 5,558,092 | A | 9/1996 | Unger et al. |
| 5,563,346 | A | 10/1996 | Bartelt et al. |
| 5,566,675 | A | 10/1996 | Li et al. |
| 5,573,497 | A | 11/1996 | Chapelon |
| 5,580,575 | A | 12/1996 | Unger et al. |
| 5,582,578 | A | 12/1996 | Zhong et al. |
| 5,590,657 | A | 1/1997 | Cain et al. |
| 5,601,526 | A | 2/1997 | Chapelon et al. |
| 5,617,862 | A | 4/1997 | Cole et al. |
| 5,648,098 | A | 7/1997 | Porter |
| 5,665,054 | A | 9/1997 | Dory |
| 5,666,954 | A | 9/1997 | Chapelon et al. |
| 5,676,452 | A | 10/1997 | Scholz |
| 5,676,692 | A | 10/1997 | Sanghvi et al. |
| 5,678,554 | A | 10/1997 | Hossack et al. |
| 5,683,064 | A | 11/1997 | Copeland et al. |
| 5,694,936 | A | 12/1997 | Fujimoto et al. |
| 5,695,460 | A | 12/1997 | Siegel et al. |
| 5,717,657 | A | 2/1998 | Ruffa |
| 5,720,287 | A | 2/1998 | Chapelon et al. |
| 5,724,972 | A | 3/1998 | Petrofsky |
| 5,743,863 | A | 4/1998 | Chapelon |
| 5,753,929 | A | 5/1998 | Bliss |
| 5,759,162 | A | 6/1998 | Oppelt et al. |
| 5,766,138 | A | 6/1998 | Rattner |
| 5,769,790 | A | 6/1998 | Watkins et al. |
| 5,797,848 | A | 8/1998 | Marian et al. |
| 5,820,623 | A | 10/1998 | Ng |
| 5,823,962 | A | 10/1998 | Schaetzle et al. |
| 5,827,204 | A | 10/1998 | Grandia et al. |
| 5,836,896 | A | 11/1998 | Rosenschein |
| 5,849,727 | A | 12/1998 | Porter et al. |
| 5,873,902 | A | 2/1999 | Sanghvi et al. |
| 5,879,314 | A | 3/1999 | Peterson et al. |
| 5,928,169 | A | 7/1999 | Schitzle et al. |
| 5,932,807 | A | 8/1999 | Mallart |
| 5,947,904 | A | 9/1999 | Hossack et al. |
| 6,001,069 | A | 12/1999 | Tachibana et al. |
| 6,007,499 | A | 12/1999 | Martin et al. |
| 6,022,309 | A | 2/2000 | Celliers et al. |
| 6,036,667 | A | 3/2000 | Manna et al. |
| 6,088,613 | A | 7/2000 | Unger |
| 6,093,883 | A | 7/2000 | Sanghvi et al. |
| 6,113,558 | A | 9/2000 | Rosenschein et al. |
| 6,126,607 | A | 10/2000 | Whitmore, III et al. |
| 6,128,958 | A | 10/2000 | Cain |
| 6,143,018 | A | 11/2000 | Beuthan et al. |
| 6,165,144 | A | 12/2000 | Talish et al. |
| 6,176,842 | B1 | 1/2001 | Tachibana et al. |
| 6,296,619 | B1 | 10/2001 | Brisken et al. |
| 6,308,585 | B1 | 10/2001 | Nilsson et al. |
| 6,308,710 | B1 | 10/2001 | Silva |
| 6,309,355 | B1 | 10/2001 | Cain et al. |
| 6,318,146 | B1 | 11/2001 | Madsen et al. |
| 6,321,109 | B2 | 11/2001 | Ben-Haim et al. |
| 6,338,566 | B1 | 1/2002 | Verdier |
| 6,344,489 | B1 | 2/2002 | Spears |

(56) References Cited

U.S. PATENT DOCUMENTS

| | | |
|---|---|---|
| 6,391,020 B1 | 5/2002 | Kurtz et al. |
| 6,413,216 B1 | 7/2002 | Cain et al. |
| 6,419,648 B1 | 7/2002 | Vitek et al. |
| 6,424,885 B1 | 7/2002 | Niemeyer et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckal et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,175,599 B2 | 2/2007 | Hynynen et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,429,249 B1 | 9/2008 | Winder et al. |
| 7,431,704 B2 | 10/2008 | Babaev |
| 7,442,168 B2 | 10/2008 | Novak et al. |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 7,695,437 B2 | 4/2010 | Quistgaard et al. |
| 7,714,481 B2 | 5/2010 | Sakai |
| 7,771,359 B2 | 8/2010 | Adam |
| 7,967,763 B2 | 6/2011 | Deem et al. |
| 8,057,408 B2 | 11/2011 | Cain et al. |
| 8,295,912 B2 | 10/2012 | Gertner |
| 8,333,115 B1 | 12/2012 | Garvey et al. |
| 8,337,407 B2 | 12/2012 | Quistgaard et al. |
| 8,342,467 B2 | 1/2013 | Stachowski et al. |
| 8,376,970 B2 | 2/2013 | Babaev |
| 8,539,813 B2 | 9/2013 | Cain et al. |
| 8,568,339 B2 | 10/2013 | Rybyanets |
| 8,636,664 B2 | 1/2014 | Brannan |
| 8,715,187 B2 | 5/2014 | Landberg Davis et al. |
| 8,845,537 B2 | 9/2014 | Tanaka et al. |
| 8,932,239 B2 | 1/2015 | Sokka et al. |
| 9,028,434 B2 | 5/2015 | Tanaka |
| 9,049,783 B2 | 6/2015 | Teofilovic |
| 9,061,131 B2 | 6/2015 | Jahnke et al. |
| 9,144,694 B2 | 9/2015 | Cain |
| 9,220,476 B2 | 12/2015 | Coussios et al. |
| 9,228,730 B1 | 1/2016 | Inbody |
| 9,302,124 B2 | 4/2016 | Konofagou et al. |
| 9,457,201 B2 | 10/2016 | Hoelscher et al. |
| 9,526,923 B2 | 12/2016 | Jahnke et al. |
| 9,636,133 B2 | 5/2017 | Hall et al. |
| 9,642,634 B2 | 5/2017 | Cain et al. |
| 9,763,688 B2 | 9/2017 | Stulen et al. |
| 9,901,753 B2 | 2/2018 | Cain et al. |
| 9,943,708 B2 | 4/2018 | Roberts et al. |
| 10,022,107 B2 | 7/2018 | Thornton et al. |
| 10,046,179 B2 | 8/2018 | Oskar-Kohler |
| 10,046,181 B2 | 8/2018 | Barthe et al. |
| 10,058,352 B2 | 8/2018 | Carvell et al. |
| 10,071,266 B2 | 9/2018 | Cain |
| 10,130,828 B2 | 11/2018 | Vortman et al. |
| 10,219,815 B2 | 3/2019 | Maxwell et al. |
| 10,293,187 B2 | 5/2019 | Cannata et al. |
| 10,751,015 B2 | 8/2020 | Anderson et al. |
| 10,751,125 B2 | 8/2020 | Levy et al. |
| 10,765,892 B1 | 9/2020 | Vitek et al. |
| 10,772,646 B2 | 9/2020 | Lu et al. |
| 10,780,298 B2 | 9/2020 | Cain et al. |
| 10,791,991 B2 | 10/2020 | Burkett et al. |
| 10,799,209 B2 | 10/2020 | Lahti et al. |
| 10,806,421 B2 | 10/2020 | Keller |
| 10,820,813 B2 | 11/2020 | Alpert |
| 10,847,264 B2 | 11/2020 | Mansker et al. |
| 10,849,511 B2 | 12/2020 | Tochterman et al. |
| 10,869,603 B2 | 12/2020 | Millett et al. |
| 10,869,633 B2 | 12/2020 | Burkett |
| 10,869,648 B2 | 12/2020 | Hubbard et al. |
| 10,874,353 B2 | 12/2020 | Assif |
| 10,874,409 B2 | 12/2020 | Matsubara et al. |
| 10,878,586 B2 | 12/2020 | Brokman et al. |
| 10,888,232 B2 | 1/2021 | Anderson et al. |
| 10,893,808 B2 | 1/2021 | Dorando |
| 10,900,933 B2 | 1/2021 | Prus et al. |
| 10,905,394 B2 | 2/2021 | Stigall et al. |
| 10,912,463 B2 | 2/2021 | Davies et al. |
| 10,925,688 B2 | 2/2021 | Millett et al. |
| 10,927,003 B2 | 2/2021 | Millett et al. |
| 10,932,678 B2 | 3/2021 | Burkett |
| 10,939,826 B2 | 3/2021 | Glynn et al. |
| 10,942,022 B2 | 3/2021 | Johansson et al. |
| 10,973,419 B2 | 4/2021 | Cori |
| 10,993,618 B2 | 5/2021 | Mansker et al. |
| 10,993,628 B2 | 5/2021 | Tochterman |
| 10,993,694 B2 | 5/2021 | Meyer et al. |
| 11,000,185 B2 | 5/2021 | Stigall et al. |
| 11,006,840 B2 | 5/2021 | Stigall |
| 11,013,491 B2 | 5/2021 | Rice et al. |
| 11,020,087 B2 | 6/2021 | Hoffman |
| 11,020,089 B2 | 6/2021 | Corl |
| 11,026,591 B2 | 6/2021 | Burkett et al. |
| 11,040,140 B2 | 6/2021 | Unser et al. |
| 11,058,399 B2 | 7/2021 | Xu et al. |
| 11,071,522 B2 | 7/2021 | Hynynen et al. |
| 11,103,731 B2 | 8/2021 | Vortman et al. |
| 11,112,473 B2 | 9/2021 | Assif |

(56) References Cited

U.S. PATENT DOCUMENTS

| | | |
|---|---|---|
| 11,119,552 B2 | 9/2021 | Spencer et al. |
| 11,120,896 B2 | 9/2021 | Balignasay et al. |
| 11,123,019 B2 | 9/2021 | Merritt et al. |
| 11,123,575 B2 | 9/2021 | Vortman et al. |
| 11,135,454 B2 | 10/2021 | Xu et al. |
| 11,141,063 B2 | 10/2021 | Kemp et al. |
| 11,141,131 B2 | 10/2021 | Stigall et al. |
| 11,160,513 B2 | 11/2021 | Anderson et al. |
| 11,205,507 B2 | 12/2021 | Anderson et al. |
| 11,219,746 B2 | 1/2022 | Burkett et al. |
| 11,224,349 B2 | 1/2022 | Davies et al. |
| 11,224,403 B2 | 1/2022 | Corl |
| 11,224,407 B2 | 1/2022 | Wrolstad et al. |
| 11,234,649 B2 | 2/2022 | Matsubara et al. |
| 11,246,533 B2 | 2/2022 | Henderson et al. |
| 11,246,565 B2 | 2/2022 | Corl |
| 11,253,225 B2 | 2/2022 | Hancock et al. |
| 11,260,160 B2 | 3/2022 | Matsubara et al. |
| 11,272,845 B2 | 3/2022 | Cheline et al. |
| 11,272,904 B2 | 3/2022 | Vortman et al. |
| 11,291,866 B2 | 4/2022 | Levy et al. |
| 11,298,030 B2 | 4/2022 | Davies et al. |
| 11,309,071 B2 | 4/2022 | Anderson |
| 11,311,271 B2 | 4/2022 | Stigall et al. |
| 11,324,410 B2 | 5/2022 | Burkett |
| 11,350,906 B2 | 6/2022 | Castella et al. |
| 11,350,954 B2 | 6/2022 | De Cicco et al. |
| 11,364,042 B2 | 6/2022 | Maxwell et al. |
| 11,369,346 B2 | 6/2022 | De Cicco et al. |
| 11,369,994 B2 | 6/2022 | Greenberg et al. |
| 11,395,638 B2 | 7/2022 | Shin et al. |
| 11,406,334 B2 | 8/2022 | Merritt |
| 11,406,355 B2 | 8/2022 | Hoffman et al. |
| 11,406,498 B2 | 8/2022 | Stigall et al. |
| 11,408,987 B2 | 8/2022 | Vignon et al. |
| 11,413,017 B2 | 8/2022 | Stigall et al. |
| 11,419,580 B2 | 8/2022 | Stigall et al. |
| 11,426,140 B2 | 8/2022 | Sudol et al. |
| 11,432,795 B2 | 9/2022 | Merritt |
| 11,432,900 B2 | 9/2022 | Rakic et al. |
| 11,446,000 B2 | 9/2022 | Minas et al. |
| 11,452,496 B2 | 9/2022 | Minas et al. |
| 11,452,506 B2 | 9/2022 | Perez et al. |
| 11,471,215 B2 | 10/2022 | Stigall et al. |
| 11,484,294 B2 | 11/2022 | Hancock et al. |
| 11,510,632 B2 | 11/2022 | Begin et al. |
| 11,517,291 B2 | 12/2022 | Kantor et al. |
| 11,520,874 B2 | 12/2022 | Kennedy et al. |
| 11,524,183 B1 | 12/2022 | Garcia Gutierrez et al. |
| 11,527,001 B2 | 12/2022 | Brokman et al. |
| 11,547,389 B2 | 1/2023 | Shin et al. |
| 11,553,889 B2 | 1/2023 | Spencer et al. |
| 11,554,386 B2 | 1/2023 | Pernot et al. |
| 11,559,207 B2 | 1/2023 | Stigall et al. |
| 11,567,153 B2 | 1/2023 | Stormont et al. |
| 11,576,649 B2 | 2/2023 | Corl |
| 11,576,652 B2 | 2/2023 | De Cicco et al. |
| 11,583,193 B2 | 2/2023 | Groenland et al. |
| 11,589,835 B2 | 2/2023 | Stigall et al. |
| 11,596,351 B2 | 3/2023 | Nair |
| 11,596,384 B2 | 3/2023 | Nair et al. |
| 11,596,385 B2 | 3/2023 | Stigall et al. |
| 11,596,387 B2 | 3/2023 | Song |
| 11,596,389 B2 | 3/2023 | Nair |
| 11,596,469 B2 | 3/2023 | Nair |
| 11,622,746 B2 | 4/2023 | Minas et al. |
| 11,638,576 B2 | 5/2023 | Groenland et al. |
| 11,647,989 B2 | 5/2023 | Hope Simpson et al. |
| 11,648,424 B2 | 5/2023 | Cannata et al. |
| 11,653,895 B2 | 5/2023 | Stigall et al. |
| 11,660,070 B2 | 5/2023 | Stigall et al. |
| 11,666,245 B2 | 6/2023 | Rajguru et al. |
| 11,666,307 B2 | 6/2023 | Unser |
| 11,672,433 B2 | 6/2023 | Park et al. |
| 11,672,552 B2 | 6/2023 | Pasquino et al. |
| 11,672,953 B2 | 6/2023 | May |
| 11,684,342 B2 | 6/2023 | Groenland et al. |
| 11,684,807 B2 | 6/2023 | Vortman et al. |
| 11,701,134 B2 | 7/2023 | Maxwell et al. |
| 11,707,207 B2 | 7/2023 | Stigall et al. |
| 11,707,254 B2 | 7/2023 | Di Tullio et al. |
| 11,733,881 B2 | 8/2023 | Perez |
| 11,737,728 B2 | 8/2023 | Davies et al. |
| 11,744,527 B2 | 9/2023 | Scott et al. |
| 11,744,547 B2 | 9/2023 | Hynynen |
| 11,759,169 B2 | 9/2023 | Cort |
| 11,759,174 B2 | 9/2023 | Saroha et al. |
| 11,766,237 B2 | 9/2023 | Anderson |
| 11,771,370 B2 | 10/2023 | Hynynen |
| 11,771,405 B2 | 10/2023 | Rhodes |
| 11,771,869 B2 | 10/2023 | Cicco |
| 11,779,307 B2 | 10/2023 | Norris et al. |
| 11,806,167 B2 | 11/2023 | Burkett |
| 11,813,484 B2 | 11/2023 | Cannata et al. |
| 11,813,485 B2 | 11/2023 | Xu et al. |
| 11,819,712 B2 | 11/2023 | Cain et al. |
| 11,854,687 B2 | 12/2023 | Keller |
| 11,857,362 B2 | 1/2024 | Wrolstad et al. |
| 11,857,807 B2 | 1/2024 | Levy et al. |
| 11,864,918 B2 | 1/2024 | Burkett et al. |
| 11,872,412 B2 | 1/2024 | Vortman et al. |
| 11,879,973 B2 | 1/2024 | Prus et al. |
| 11,883,235 B2 | 1/2024 | Stigall et al. |
| 11,890,025 B2 | 2/2024 | Stigall et al. |
| 11,890,136 B2 | 2/2024 | Stigall et al. |
| 11,890,137 B2 | 2/2024 | Jenkins et al. |
| 11,950,954 B2 | 4/2024 | Hyun et al. |
| 11,963,822 B2 | 4/2024 | Wrolstad |
| 11,986,682 B2 | 5/2024 | Prus et al. |
| 11,992,366 B2 | 5/2024 | Stigall et al. |
| 12,017,013 B2 | 6/2024 | Sasamine et al. |
| 12,035,919 B2 | 7/2024 | Unser |
| 12,036,066 B2 | 7/2024 | De Cicco et al. |
| 12,053,194 B2 | 8/2024 | Goertz et al. |
| 12,082,970 B2 | 9/2024 | Goodman |
| 12,096,949 B2 | 9/2024 | Fermi et al. |
| 12,097,072 B2 | 9/2024 | Stigall et al. |
| 12,112,850 B2 | 10/2024 | Kuo et al. |
| 12,115,007 B2 | 10/2024 | Merritt et al. |
| 12,144,677 B2 | 11/2024 | Corl |
| 12,167,931 B2 | 12/2024 | Corl |
| 12,178,642 B2 | 12/2024 | Rajguru et al. |
| 12,178,643 B2 | 12/2024 | Stigall et al. |
| 12,186,130 B2 | 1/2025 | Davies |
| 12,220,259 B2 | 2/2025 | Burkett et al. |
| 12,232,907 B2 | 2/2025 | Chao et al. |
| 12,246,195 B2 | 3/2025 | Levy et al. |
| 12,440,188 B2 | 10/2025 | Chao et al. |
| 12,465,477 B2 | 11/2025 | Pasquino et al. |
| 2001/0039420 A1 | 11/2001 | Burbank et al. |
| 2001/0041163 A1 | 11/2001 | Sugita |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2002/0145091 A1 | 10/2002 | Talish et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0169591 A1 | 9/2003 | Cochran |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0162571 A1 | 8/2004 | Rabiner et al. |
| 2004/0164213 A1 | 8/2004 | Stephan |
| 2004/0236248 A1 | 11/2004 | Svedman |
| 2004/0243021 A1 | 12/2004 | Murphy et al. |
| 2004/0249509 A1 | 12/2004 | Rogers et al. |
| 2004/0260214 A1 | 12/2004 | Echt et al. |
| 2005/0011296 A1 | 1/2005 | Koseki |
| 2005/0020945 A1 | 1/2005 | Tosaya et al. |

(56)        References Cited

U.S. PATENT DOCUMENTS

| | | |
|---|---|---|
| 2005/0038339 A1 | 2/2005 | Chauhan et al. |
| 2005/0038361 A1 | 2/2005 | Zhong et al. |
| 2005/0152561 A1 | 7/2005 | Spencer |
| 2005/0154314 A1 | 7/2005 | Quistgaard |
| 2005/0154431 A1 | 7/2005 | Quistgaard et al. |
| 2005/0203399 A1 | 9/2005 | Vaezy et al. |
| 2005/0215901 A1 | 9/2005 | Anderson et al. |
| 2005/0234438 A1 | 10/2005 | Mast et al. |
| 2005/0283098 A1 | 12/2005 | Conston et al. |
| 2006/0058678 A1 | 3/2006 | Vitek et al. |
| 2006/0060991 A1 | 3/2006 | Holsteyns et al. |
| 2006/0074303 A1 | 4/2006 | Chornenky et al. |
| 2006/0089636 A1 | 4/2006 | Christopherson et al. |
| 2006/0173321 A1 | 8/2006 | Kubota et al. |
| 2006/0173387 A1 | 8/2006 | Hansmann et al. |
| 2006/0184166 A1 | 8/2006 | Valle et al. |
| 2006/0206028 A1 | 9/2006 | Lee et al. |
| 2006/0229659 A1 | 10/2006 | Gifford et al. |
| 2006/0241466 A1 | 10/2006 | Ottoboni et al. |
| 2006/0241523 A1 | 10/2006 | Sinelnikov et al. |
| 2006/0241533 A1 | 10/2006 | Geller |
| 2006/0264760 A1 | 11/2006 | Liu et al. |
| 2006/0293598 A1 | 12/2006 | Fraser |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |
| 2007/0083120 A1 | 4/2007 | Cain et al. |
| 2007/0140413 A1 | 6/2007 | Saracen |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2007/0239001 A1 | 10/2007 | Mehl et al. |
| 2008/0013593 A1 | 1/2008 | Kawabata |
| 2008/0033297 A1 | 2/2008 | Sliwa |
| 2008/0033417 A1 | 2/2008 | Nields et al. |
| 2008/0051656 A1 | 2/2008 | Vaezy et al. |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0154132 A1 | 6/2008 | Hall et al. |
| 2008/0167555 A1 | 7/2008 | Qian et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0300485 A1 | 12/2008 | Liu et al. |
| 2008/0312561 A1 | 12/2008 | Chauhan |
| 2008/0319376 A1 | 12/2008 | Wilcox et al. |
| 2009/0012514 A1 | 1/2009 | Moonen et al. |
| 2009/0030339 A1 | 1/2009 | Cheng et al. |
| 2009/0036773 A1 | 2/2009 | Lau et al. |
| 2009/0112098 A1 | 4/2009 | Vaezy et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2009/0254008 A1 | 10/2009 | Shields, Jr. |
| 2009/0287083 A1 | 11/2009 | Kushculey et al. |
| 2009/0306502 A1 | 12/2009 | Lacoste |
| 2010/0011845 A1 | 1/2010 | Laugharn et al. |
| 2010/0042020 A1 | 2/2010 | Ben-Ezra |
| 2010/0056924 A1 | 3/2010 | Powers |
| 2010/0059264 A1 | 3/2010 | Hasegawa et al. |
| 2010/0069797 A1 | 3/2010 | Cain et al. |
| 2010/0125225 A1 | 5/2010 | Gelbart et al. |
| 2010/0152624 A1 | 6/2010 | Tanis et al. |
| 2010/0163694 A1 | 7/2010 | Fadler et al. |
| 2010/0204578 A1 | 8/2010 | Schmidt et al. |
| 2010/0261994 A1 | 10/2010 | Davalos et al. |
| 2010/0274136 A1 | 10/2010 | Cerofolini |
| 2010/0286519 A1 | 11/2010 | Lee et al. |
| 2010/0298744 A1 | 11/2010 | Altshuler et al. |
| 2010/0305432 A1 | 12/2010 | Duhay et al. |
| 2010/0317971 A1 | 12/2010 | Fan et al. |
| 2010/0318002 A1 | 12/2010 | Prus et al. |
| 2011/0072970 A1 | 3/2011 | Slobodzian et al. |
| 2011/0112400 A1 | 5/2011 | Emery et al. |
| 2011/0118600 A1 | 5/2011 | Gertner |
| 2011/0118602 A1 | 5/2011 | Weng et al. |
| 2011/0144490 A1 | 6/2011 | Davis et al. |
| 2011/0144545 A1 | 6/2011 | Fan et al. |
| 2011/0172529 A1 | 7/2011 | Gertner |
| 2011/0178444 A1 | 7/2011 | Slayton et al. |
| 2011/0245671 A1 | 10/2011 | Sato |
| 2011/0251528 A1 | 10/2011 | Canney et al. |
| 2011/0257524 A1 | 10/2011 | Gertner |
| 2011/0257561 A1* | 10/2011 | Gertner ............... A61B 5/4035 |
| | | 600/407 |
| 2011/0263967 A1 | 10/2011 | Bailey et al. |
| 2011/0270136 A1 | 11/2011 | Vitek et al. |
| 2011/0319765 A1* | 12/2011 | Gertner ................... A61N 7/02 |
| | | 600/453 |
| 2011/0319927 A1 | 12/2011 | Nita |
| 2012/0029337 A1 | 2/2012 | Aoyagi |
| 2012/0029353 A1 | 2/2012 | Slayton et al. |
| 2012/0029393 A1 | 2/2012 | Lee |
| 2012/0059264 A1 | 3/2012 | Hope Simpson et al. |
| 2012/0059285 A1 | 3/2012 | Soltani et al. |
| 2012/0065492 A1* | 3/2012 | Gertner ................... A61B 8/08 |
| | | 601/2 |
| 2012/0065493 A1* | 3/2012 | Gertner ............... A61N 5/0622 |
| | | 604/23 |
| 2012/0065494 A1* | 3/2012 | Gertner ................... A61B 8/06 |
| | | 601/2 |
| 2012/0092724 A1 | 4/2012 | Pettis |
| 2012/0111339 A1 | 5/2012 | Barthe et al. |
| 2012/0130288 A1 | 5/2012 | Holland et al. |
| 2012/0136279 A1 | 5/2012 | Tanaka et al. |
| 2012/0158013 A1 | 6/2012 | Stefanchik et al. |
| 2012/0172720 A1 | 7/2012 | Asami et al. |
| 2012/0189998 A1 | 7/2012 | Kruecker et al. |
| 2012/0215157 A1 | 8/2012 | Berryman et al. |
| 2012/0232388 A1 | 9/2012 | Curra et al. |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2012/0281902 A1 | 11/2012 | Oikawa et al. |
| 2013/0051178 A1 | 2/2013 | Rybyanets |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0144165 A1 | 6/2013 | Ebbini et al. |
| 2013/0172739 A1 | 7/2013 | Paladini |
| 2013/0190623 A1 | 7/2013 | Bertolina et al. |
| 2013/0190661 A1 | 7/2013 | Wing et al. |
| 2013/0255426 A1 | 10/2013 | Kassow et al. |
| 2013/0303906 A1 | 11/2013 | Cain et al. |
| 2014/0030806 A1 | 1/2014 | Dudley et al. |
| 2014/0039358 A1 | 2/2014 | Zhou et al. |
| 2014/0046181 A1 | 2/2014 | Benchimol et al. |
| 2014/0058293 A1 | 2/2014 | Hynynen et al. |
| 2014/0058294 A1 | 2/2014 | Gross et al. |
| 2014/0073995 A1 | 3/2014 | Teofilovic et al. |
| 2014/0074076 A1* | 3/2014 | Gertner ................... A61B 6/12 |
| | | 606/169 |
| 2014/0088613 A1 | 3/2014 | Seo et al. |
| 2014/0100459 A1 | 4/2014 | Xu et al. |
| 2014/0112107 A1 | 4/2014 | Guo et al. |
| 2014/0128734 A1 | 5/2014 | Genstler et al. |
| 2014/0200489 A1 | 7/2014 | Behar et al. |
| 2014/0243664 A1 | 8/2014 | El-Sayed et al. |
| 2014/0316269 A1 | 10/2014 | Zhang et al. |
| 2014/0324034 A1 | 10/2014 | Assaf et al. |
| 2014/0330124 A1 | 11/2014 | Carol |
| 2014/0378832 A1 | 12/2014 | Sanghvi et al. |
| 2014/0378964 A1 | 12/2014 | Pearson |
| 2015/0011875 A1 | 1/2015 | Noordhoek et al. |
| 2015/0063668 A1 | 3/2015 | You et al. |
| 2015/0073261 A1 | 3/2015 | Kohler et al. |

(56)                    References Cited

U.S. PATENT DOCUMENTS

| | | |
|---|---|---|
| 2015/0080926 A1 | 3/2015 | Emery |
| 2015/0148659 A1 | 5/2015 | Vahala |
| 2015/0151141 A1 | 6/2015 | Arnal et al. |
| 2015/0190121 A1 | 7/2015 | Slayton et al. |
| 2015/0190659 A1 | 7/2015 | Kolher |
| 2015/0196239 A1 | 7/2015 | Meehan et al. |
| 2015/0224347 A1 | 8/2015 | Barthe et al. |
| 2015/0257779 A1 | 9/2015 | Sinelnikov et al. |
| 2015/0258352 A1 | 9/2015 | Lin et al. |
| 2015/0265243 A1 | 9/2015 | Kelly |
| 2015/0273246 A1 | 10/2015 | Darlington et al. |
| 2015/0297177 A1 | 10/2015 | Boctor et al. |
| 2016/0004933 A1 | 1/2016 | Hu et al. |
| 2016/0038665 A1 | 2/2016 | Schaefer et al. |
| 2016/0114194 A1 | 4/2016 | Gertner |
| 2016/0120572 A1 | 5/2016 | Lee |
| 2016/0135782 A1 | 5/2016 | Chen et al. |
| 2016/0151618 A1 | 6/2016 | Powers et al. |
| 2016/0184614 A1 | 6/2016 | Matula et al. |
| 2016/0184616 A1* | 6/2016 | Cain ........................ A61N 7/00 |
| | | 601/2 |
| 2016/0206341 A1 | 7/2016 | Slayton |
| 2016/0206867 A1 | 7/2016 | Hossack et al. |
| 2016/0249859 A1 | 9/2016 | Babkin et al. |
| 2016/0287909 A1 | 10/2016 | Maxwell et al. |
| 2016/0303166 A1 | 10/2016 | Katz et al. |
| 2016/0331583 A1 | 11/2016 | Geringer |
| 2016/0331585 A1 | 11/2016 | Kim |
| 2016/0339273 A1 | 11/2016 | Al Mayiah |
| 2016/0345938 A1 | 12/2016 | Tanter et al. |
| 2016/0354087 A1 | 12/2016 | Noonan et al. |
| 2016/0361574 A1 | 12/2016 | Barthe et al. |
| 2017/0000376 A1 | 1/2017 | Partanen et al. |
| 2017/0049463 A1 | 2/2017 | Popovic et al. |
| 2017/0071515 A1 | 3/2017 | Chevillet et al. |
| 2017/0072227 A1 | 3/2017 | Khokhlova et al. |
| 2017/0072228 A1 | 3/2017 | Wang et al. |
| 2017/0100145 A1 | 4/2017 | Khoklova et al. |
| 2017/0120080 A1 | 5/2017 | Phillips et al. |
| 2017/0165046 A1 | 6/2017 | Johnson et al. |
| 2017/0183062 A1 | 6/2017 | Lee |
| 2017/0197099 A1 | 7/2017 | Ruebel et al. |
| 2017/0232277 A1 | 8/2017 | Hall et al. |
| 2017/0263846 A1 | 9/2017 | Nakamura et al. |
| 2017/0281983 A1 | 10/2017 | Marquet et al. |
| 2018/0000444 A1 | 1/2018 | Dayton et al. |
| 2018/0008787 A1 | 1/2018 | Schriver et al. |
| 2018/0028841 A1 | 2/2018 | Konofagou et al. |
| 2018/0064412 A1 | 3/2018 | Messas et al. |
| 2018/0154186 A1* | 6/2018 | Xu ............................ A61N 7/02 |
| 2018/0161086 A1 | 6/2018 | Davalos et al. |
| 2018/0169444 A1 | 6/2018 | Averkiou et al. |
| 2018/0206816 A1 | 7/2018 | Prus et al. |
| 2018/0236271 A1 | 8/2018 | Tanter et al. |
| 2018/0317884 A1 | 11/2018 | Chapelon et al. |
| 2018/0374471 A1 | 12/2018 | Dirksen et al. |
| 2019/0000422 A1 | 1/2019 | West et al. |
| 2019/0023804 A1 | 1/2019 | Onik et al. |
| 2019/0082998 A1 | 3/2019 | Nowroozi et al. |
| 2019/0275353 A1 | 9/2019 | Cannata et al. |
| 2019/0282294 A1 | 9/2019 | Davalos et al. |
| 2019/0314045 A1 | 10/2019 | Cunitz et al. |
| 2019/0320904 A1 | 10/2019 | Mei |
| 2019/0323086 A1 | 10/2019 | Leuthardt et al. |
| 2019/0328500 A1 | 10/2019 | Cichon et al. |
| 2020/0010575 A1 | 1/2020 | Hode et al. |
| 2020/0055085 A1 | 2/2020 | Taffler |
| 2020/0078608 A1 | 3/2020 | Maxwell et al. |
| 2020/0107843 A1 | 4/2020 | Goertz et al. |
| 2020/0164231 A1* | 5/2020 | Cannata ................... A61N 7/00 |
| 2020/0182989 A1 | 6/2020 | Freeman et al. |
| 2020/0194117 A1 | 6/2020 | Krieger et al. |
| 2020/0253550 A1 | 8/2020 | Nair |
| 2020/0254285 A1 | 8/2020 | Jang et al. |
| 2020/0260964 A1 | 8/2020 | Collins et al. |
| 2020/0282239 A1 | 9/2020 | Beder et al. |
| 2020/0289080 A1 | 9/2020 | Yang et al. |
| 2020/0305842 A1 | 10/2020 | Rosenzweig et al. |
| 2020/0323515 A1 | 10/2020 | Levy |
| 2020/0330039 A1 | 10/2020 | Burkett et al. |
| 2020/0330075 A1 | 10/2020 | O'Reilly et al. |
| 2020/0346044 A1* | 11/2020 | Woodacre ............... B06B 1/067 |
| 2020/0353293 A1 | 11/2020 | Khokhlova et al. |
| 2020/0367835 A1 | 11/2020 | Anderson |
| 2020/0375576 A1 | 12/2020 | Moulton |
| 2020/0405258 A1 | 12/2020 | Dayton et al. |
| 2020/0405259 A1 | 12/2020 | Merritt |
| 2021/0000541 A1 | 1/2021 | Levy et al. |
| 2021/0009936 A1 | 1/2021 | Kamen et al. |
| 2021/0022703 A1 | 1/2021 | Nair |
| 2021/0022714 A1 | 1/2021 | Zagrodsky et al. |
| 2021/0100527 A1 | 4/2021 | Martin |
| 2021/0108866 A1 | 4/2021 | Lucht et al. |
| 2021/0161398 A1 | 6/2021 | Millett et al. |
| 2021/0169515 A1 | 6/2021 | Pahk et al. |
| 2021/0170204 A1 | 6/2021 | Vortman et al. |
| 2021/0170205 A1 | 6/2021 | Vortman et al. |
| 2021/0187331 A1 | 6/2021 | Zadicario et al. |
| 2021/0196295 A1 | 7/2021 | Goudot et al. |
| 2021/0220607 A1 | 7/2021 | Sasamine et al. |
| 2021/0252313 A1* | 8/2021 | Xu ..................... A61B 10/0233 |
| 2021/0330294 A1 | 10/2021 | Hynynen et al. |
| 2021/0353161 A1 | 11/2021 | Merritt et al. |
| 2021/0386451 A1 | 12/2021 | Escudero et al. |
| 2021/0401400 A1 | 12/2021 | Sheehan et al. |
| 2022/0008036 A1 | 1/2022 | Gulsen et al. |
| 2022/0022845 A1 | 1/2022 | Corl |
| 2022/0031287 A1 | 2/2022 | Ebbini et al. |
| 2022/0043143 A1 | 2/2022 | Prus et al. |
| 2022/0079563 A1 | 3/2022 | Kemp |
| 2022/0087640 A1 | 3/2022 | Minas et al. |
| 2022/0166462 A1 | 5/2022 | Deurenberg et al. |
| 2022/0167920 A1 | 6/2022 | Margolis |
| 2022/0168470 A1 | 6/2022 | Ricotti et al. |
| 2022/0196771 A1 | 6/2022 | Zur et al. |
| 2022/0202483 A1* | 6/2022 | Gertner ................... A61N 7/00 |
| 2022/0203139 A1 | 6/2022 | Shapira |
| 2022/0219019 A1 | 7/2022 | Xu et al. |
| 2022/0233890 A1 | 7/2022 | Hynynen et al. |
| 2022/0240890 A1 | 8/2022 | Hancock et al. |
| 2022/0257329 A1 | 8/2022 | Stigall et al. |
| 2022/0280233 A1 | 9/2022 | Park et al. |
| 2022/0280367 A1 | 9/2022 | Diodato et al. |
| 2022/0296211 A1 | 9/2022 | Saroha et al. |
| 2022/0338750 A1 | 10/2022 | Allen et al. |
| 2022/0346756 A1 | 11/2022 | Chen |
| 2022/0395333 A1 | 12/2022 | Merritt et al. |
| 2022/0409858 A1 | 12/2022 | Lin |
| 2023/0000466 A1 | 1/2023 | Levy et al. |
| 2023/0000469 A1 | 1/2023 | Prus et al. |
| 2023/0008714 A1 | 1/2023 | Rajguru et al. |
| 2023/0012365 A1 | 1/2023 | Alpert et al. |
| 2023/0024998 A1 | 1/2023 | Greenberg |
| 2023/0037603 A1 | 2/2023 | Pombo et al. |
| 2023/0038498 A1* | 2/2023 | Xu ........................ A61B 34/30 |
| 2023/0038543 A1 | 2/2023 | Minas et al. |
| 2023/0042834 A1 | 2/2023 | Henderson et al. |
| 2023/0045488 A1 | 2/2023 | Rajguru et al. |
| 2023/0048979 A1 | 2/2023 | Lindenmoyer et al. |
| 2023/0050732 A1 | 2/2023 | Hancock et al. |
| 2023/0061534 A1* | 3/2023 | Stopek ................... A61B 34/25 |
| 2023/0073477 A1 | 3/2023 | Minas et al. |
| 2023/0100912 A1 | 3/2023 | Amar et al. |
| 2023/0112722 A1 | 4/2023 | Hoffman et al. |
| 2023/0114972 A1 | 4/2023 | Bigham et al. |
| 2023/0126520 A1* | 4/2023 | Lenich ................... A61B 34/10 |
| | | 606/29 |
| 2023/0145064 A1 | 5/2023 | Vortman et al. |
| 2023/0218269 A1 | 7/2023 | Alpert et al. |
| 2023/0218930 A1* | 7/2023 | Stopek ................... A61B 8/085 |
| | | 601/3 |
| 2023/0240615 A1 | 8/2023 | May et al. |
| 2023/0240792 A1 | 8/2023 | Rakic et al. |
| 2023/0270388 A1 | 8/2023 | Richardson et al. |

(56) References Cited

U.S. PATENT DOCUMENTS

| 2023/0310899 A1 | 10/2023 | Hall et al. |
| 2023/0310900 A1 | 10/2023 | Cannata et al. |
| 2023/0310901 A1 | 10/2023 | Cannata et al. |
| 2023/0329559 A1 | 10/2023 | Xu et al. |
| 2023/0334659 A1 | 10/2023 | Marama et al. |
| 2023/0334677 A1 | 10/2023 | Sturm |
| 2023/0338010 A1 | 10/2023 | Sturm |
| 2023/0372025 A1 | 11/2023 | Van der Zaag et al. |
| 2023/0381544 A1 | 11/2023 | Penot et al. |
| 2023/0389891 A1 | 12/2023 | Cohen et al. |
| 2023/0398381 A1 | 12/2023 | Vitek et al. |
| 2024/0000422 A1 | 1/2024 | Corl |
| 2024/0000426 A1 | 1/2024 | Davies et al. |
| 2024/0001157 A1 | 1/2024 | Cannata et al. |
| 2024/0001158 A1 | 1/2024 | Cannata et al. |
| 2024/0023928 A1 | 1/2024 | Di Tullio et al. |
| 2024/0023930 A1 | 1/2024 | Anderson |
| 2024/0023941 A1 | 1/2024 | Rhodes |
| 2024/0024705 A1 | 1/2024 | Xu et al. |
| 2024/0033542 A1 | 2/2024 | Cain et al. |
| 2024/0065632 A1 | 2/2024 | Burkett |
| 2024/0138807 A1 | 5/2024 | Minas |
| 2024/0139552 A1* | 5/2024 | Duryea .................. A61B 34/10 |
| 2024/0139553 A1* | 5/2024 | Miller ................... B06B 1/0215 |
| 2024/0165666 A1 | 5/2024 | Hynynen et al. |
| 2024/0188929 A1 | 6/2024 | Minas et al. |
| 2024/0188931 A1 | 6/2024 | Ossmann et al. |
| 2024/0189627 A1* | 6/2024 | Bogott ............... A61B 17/2251 |
| 2024/0189628 A1* | 6/2024 | Grumbir ............ A61B 17/2251 |
| 2024/0207654 A1* | 6/2024 | Xu .......................... B33Y 80/00 |
| 2024/0225592 A1 | 7/2024 | May et al. |
| 2024/0245374 A1 | 7/2024 | Jenkins et al. |
| 2024/0245390 A1 | 7/2024 | Winkler Brown et al. |
| 2024/0245465 A1 | 7/2024 | Jenkins et al. |
| 2024/0285249 A1 | 8/2024 | May |
| 2024/0299092 A1 | 9/2024 | Boinagrov et al. |
| 2024/0307027 A1 | 9/2024 | Minas |
| 2024/0335680 A1 | 10/2024 | Achrol et al. |
| 2024/0341732 A1 | 10/2024 | Hoffman et al. |
| 2024/0350118 A1 | 10/2024 | Jenkins et al. |
| 2024/0350153 A1* | 10/2024 | Cannata .................. A61B 8/461 |
| 2024/0374242 A1 | 11/2024 | Merritt et al. |
| 2025/0040912 A1 | 2/2025 | Levy et al. |
| 2025/0041577 A1 | 2/2025 | Shapira et al. |
| 2025/0072872 A1 | 3/2025 | Nachtomy et al. |
| 2025/0090871 A1* | 3/2025 | Snell ........................ A61N 7/00 |

FOREIGN PATENT DOCUMENTS

| BR | 112018017326 B1 | 12/2022 |
| CA | 3073552 A1 | 3/2019 |
| CA | 3101381 A1 | 11/2019 |
| CA | 3055856 A1 | 4/2020 |
| CA | 3153080 A1 | 4/2021 |
| CA | 2910561 C | 7/2021 |
| CA | 2908740 C | 10/2021 |
| CA | 2980976 C | 3/2023 |
| CA | 2840014 C | 8/2023 |
| CN | 1669672 A | 9/2005 |
| CN | 1732031 A | 2/2006 |
| CN | 201197744 Y | 2/2009 |
| CN | 102292123 A | 12/2011 |
| CN | 102481164 A | 5/2012 |
| CN | 102665585 A | 9/2012 |
| CN | 103537016 A | 1/2014 |
| CN | 103648361 A | 3/2014 |
| CN | 103812477 A | 5/2014 |
| CN | 104013444 A | 9/2014 |
| CN | 104135938 A | 11/2014 |
| CN | 104208822 A | 12/2014 |
| CN | 106999076 B | 8/2017 |
| CN | 109185113 A | 1/2019 |
| CN | 109219415 A | 1/2019 |
| CN | 109689160 A | 4/2019 |
| CN | 208725992 U | 4/2019 |
| CN | 111565642 A | 8/2020 |
| CN | 111655337 A | 9/2020 |
| CN | 111699022 A | 9/2020 |
| CN | 111712300 A | 9/2020 |
| CN | 111712301 A | 9/2020 |
| CN | 106999053 B | 10/2020 |
| CN | 107660137 B | 10/2020 |
| CN | 111757769 A | 10/2020 |
| CN | 112204412 A | 1/2021 |
| CN | 112236195 A | 1/2021 |
| CN | 106661535 B | 3/2021 |
| CN | 112533673 A | 3/2021 |
| CN | 112566694 A | 3/2021 |
| CN | 106999054 B | 5/2021 |
| CN | 106793997 B | 6/2021 |
| CN | 107530049 B | 6/2021 |
| CN | 112912011 A | 6/2021 |
| CN | 112912012 A | 6/2021 |
| CN | 112912013 A | 6/2021 |
| CN | 112969413 A | 6/2021 |
| CN | 112996445 A | 6/2021 |
| CN | 113167877 A | 7/2021 |
| CN | 113196080 A | 7/2021 |
| CN | 109196369 B | 8/2021 |
| CN | 109200484 B | 8/2021 |
| CN | 113316419 A | 8/2021 |
| CN | 113329788 A | 8/2021 |
| CN | 109640830 B | 10/2021 |
| CN | 113473917 A | 10/2021 |
| CN | 113507946 A | 10/2021 |
| CN | 113518588 A | 10/2021 |
| CN | 113705586 A | 11/2021 |
| CN | 110662575 B | 12/2021 |
| CN | 113905666 A | 1/2022 |
| CN | 114222536 A | 3/2022 |
| CN | 114366154 A | 4/2022 |
| CN | 114423362 A | 4/2022 |
| CN | 110248606 B | 6/2022 |
| CN | 115227992 A | 10/2022 |
| CN | 109843181 B | 11/2022 |
| CN | 115461000 A | 12/2022 |
| CN | 115515504 A | 12/2022 |
| CN | 109091768 B | 3/2023 |
| CN | 115779285 A | 3/2023 |
| CN | 115779287 A | 3/2023 |
| CN | 115813438 A | 3/2023 |
| CN | 111032157 B | 4/2023 |
| CN | 115916035 A | 4/2023 |
| CN | 110958858 B | 5/2023 |
| CN | 116172611 A | 5/2023 |
| CN | 111655337 B | 6/2023 |
| CN | 109416908 B | 7/2023 |
| CN | 116507295 A | 7/2023 |
| CN | 107529989 B | 8/2023 |
| CN | 111372522 B | 8/2023 |
| CN | 116617589 A | 8/2023 |
| CN | 112236195 B | 9/2023 |
| CN | 113615098 B | 9/2023 |
| CN | 114555247 B | 9/2023 |
| CN | 116744856 A | 9/2023 |
| CN | 116761554 A | 9/2023 |
| CN | 109416907 B | 10/2023 |
| CN | 117295467 A | 12/2023 |
| CN | 117321444 A | 12/2023 |
| CN | 117337151 A | 1/2024 |
| CN | 117500437 A | 2/2024 |
| CN | 117580499 A | 2/2024 |
| CN | 111212606 B | 3/2024 |
| CN | 113490459 B | 5/2024 |
| CN | 118042992 A | 5/2024 |
| CN | 118414127 A | 7/2024 |
| CN | 112601498 B | 9/2024 |
| CN | 118678921 A | 9/2024 |
| CN | 113271866 B | 10/2024 |
| CN | 112603273 B | 12/2024 |
| CN | 112639754 B | 12/2024 |
| CN | 119367006 A | 1/2025 |
| CN | 112704620 B | 2/2025 |
| CN | 114287963 B | 2/2025 |

(56) References Cited

FOREIGN PATENT DOCUMENTS

| | | | |
|---|---|---|---|
| CN | 112494106 | B | 10/2025 |
| CN | 114638798 | B | 10/2025 |
| DE | 3220751 | A1 | 12/1983 |
| DE | 3544628 | A1 | 6/1987 |
| DE | 3817094 | A1 | 11/1989 |
| DE | 4012760 | A1 | 5/1992 |
| DE | 602020059056 | T2 | 9/2025 |
| DE | 602017092008 | T2 | 10/2025 |
| EP | 0017382 | A1 | 10/1980 |
| EP | 0320303 | A2 | 6/1989 |
| EP | 0332871 | A2 | 9/1989 |
| EP | 0384831 | A2 | 8/1990 |
| EP | 0755653 | A1 | 1/1997 |
| EP | 1374785 | A1 | 1/2004 |
| EP | 1504713 | A1 | 2/2005 |
| EP | 1566201 | A2 | 8/2005 |
| EP | 2397188 | A1 | 12/2011 |
| EP | 2934308 | B1 | 10/2015 |
| EP | 2934309 | B1 | 10/2015 |
| EP | 3097180 | B1 | 11/2016 |
| EP | 2759003 | B1 | 8/2020 |
| EP | 3558457 | A4 | 8/2020 |
| EP | 3700629 | A1 | 9/2020 |
| EP | 3218829 | B1 | 10/2020 |
| EP | 3229688 | B1 | 10/2020 |
| EP | 3723857 | A1 | 10/2020 |
| EP | 2887989 | B1 | 2/2021 |
| EP | 3777689 | A1 | 2/2021 |
| EP | 2938253 | B1 | 3/2021 |
| EP | 3076864 | B1 | 3/2021 |
| EP | 2802276 | B1 | 4/2021 |
| EP | 2809221 | B1 | 4/2021 |
| EP | 3801761 | A1 | 4/2021 |
| EP | 3801762 | A2 | 4/2021 |
| EP | 3801763 | A1 | 4/2021 |
| EP | 2967369 | B1 | 5/2021 |
| EP | 2967488 | B1 | 6/2021 |
| EP | 3184048 | B1 | 6/2021 |
| EP | 2967370 | B1 | 9/2021 |
| EP | 3482390 | B1 | 9/2021 |
| EP | 3870067 | A1 | 9/2021 |
| EP | 3870069 | A1 | 9/2021 |
| EP | 3876843 | A1 | 9/2021 |
| EP | 2931130 | B1 | 10/2021 |
| EP | 2934304 | B1 | 10/2021 |
| EP | 3887843 | A1 | 10/2021 |
| EP | 3888534 | A1 | 10/2021 |
| EP | 3895604 | A1 | 10/2021 |
| EP | 3897391 | A1 | 10/2021 |
| EP | 3229672 | B1 | 11/2021 |
| EP | 3902603 | A1 | 11/2021 |
| EP | 3903672 | A1 | 11/2021 |
| EP | 2964096 | B1 | 12/2021 |
| EP | 3930776 | A1 | 1/2022 |
| EP | 3545829 | B1 | 3/2022 |
| EP | 3959530 | A2 | 3/2022 |
| EP | 3060129 | B1 | 4/2022 |
| EP | 3986296 | A1 | 4/2022 |
| EP | 3988167 | A1 | 4/2022 |
| EP | 2914166 | B1 | 5/2022 |
| EP | 3229674 | B1 | 5/2022 |
| EP | 2779907 | B1 | 6/2022 |
| EP | 3102098 | B1 | 6/2022 |
| EP | 2965263 | B1 | 7/2022 |
| EP | 2726152 | B1 | 8/2022 |
| EP | 4041387 | A1 | 8/2022 |
| EP | 4042936 | A1 | 8/2022 |
| EP | 3298959 | B2 | 9/2022 |
| EP | 2931131 | B1 | 11/2022 |
| EP | 2938268 | B1 | 11/2022 |
| EP | 3581103 | B1 | 11/2022 |
| EP | 4087492 | A1 | 11/2022 |
| EP | 4093470 | A1 | 11/2022 |
| EP | 3091905 | B1 | 12/2022 |
| EP | 4098203 | A1 | 12/2022 |
| EP | 2950737 | B1 | 1/2023 |
| EP | 3057496 | B1 | 1/2023 |
| EP | 4114274 | A1 | 1/2023 |
| EP | 4117534 | A1 | 1/2023 |
| EP | 2869804 | B1 | 2/2023 |
| EP | 2938265 | B1 | 2/2023 |
| EP | 3024403 | B1 | 3/2023 |
| EP | 4138672 | A1 | 3/2023 |
| EP | 4151156 | A1 | 3/2023 |
| EP | 2938271 | B1 | 4/2023 |
| EP | 4161360 | A1 | 4/2023 |
| EP | 4179995 | A2 | 5/2023 |
| EP | 3171764 | B1 | 6/2023 |
| EP | 2931132 | B1 | 7/2023 |
| EP | 3229695 | B1 | 7/2023 |
| EP | 4226864 | A1 | 8/2023 |
| EP | 4230121 | A2 | 8/2023 |
| EP | 4230146 | A1 | 8/2023 |
| EP | 4233972 | A2 | 8/2023 |
| EP | 2866733 | B1 | 9/2023 |
| EP | 3870069 | B1 | 9/2023 |
| EP | 4247489 | A1 | 9/2023 |
| EP | 3484371 | B1 | 10/2023 |
| EP | 3658037 | B1 | 10/2023 |
| EP | 3685874 | B1 | 10/2023 |
| EP | 3870070 | B1 | 10/2023 |
| EP | 2938255 | B1 | 11/2023 |
| EP | 3229906 | B1 | 11/2023 |
| EP | 3764914 | B1 | 11/2023 |
| EP | 3903672 | B1 | 11/2023 |
| EP | 4272654 | A2 | 11/2023 |
| EP | 4275609 | A2 | 11/2023 |
| EP | 3316804 | B1 | 12/2023 |
| EP | 3519109 | B1 | 12/2023 |
| EP | 3166479 | B1 | 1/2024 |
| EP | 3537984 | B1 | 1/2024 |
| EP | 3908195 | B1 | 2/2024 |
| EP | 3182920 | B1 | 3/2024 |
| EP | 3174643 | B1 | 4/2024 |
| EP | 3814917 | B1 | 4/2024 |
| EP | 4349283 | A1 | 4/2024 |
| EP | 3681419 | B1 | 5/2024 |
| EP | 4368118 | A2 | 5/2024 |
| EP | 2804525 | B1 | 6/2024 |
| EP | 4380667 | A2 | 6/2024 |
| EP | 3324836 | B1 | 9/2024 |
| EP | 3624732 | B1 | 11/2024 |
| EP | 4289415 | A4 | 1/2025 |
| EP | 3190958 | B1 | 2/2025 |
| ES | 2774069 | T3 | 7/2020 |
| ES | 2819552 | T3 | 4/2021 |
| ES | 2829822 | T3 | 6/2021 |
| ES | 2998435 | T3 | 2/2025 |
| GB | 2099582 | A | 12/1982 |
| HK | 1245715 | B | 1/2021 |
| IL | L254768 | A | 5/2021 |
| IL | 261285 | B | 2/2022 |
| IL | 445766 | B | 8/2023 |
| IN | 202117039853 | A | 12/2021 |
| IN | 387413 | B | 1/2022 |
| JP | 60-80779 | A | 5/1985 |
| JP | 61-196718 | A | 8/1986 |
| JP | S62144641 | A | 6/1987 |
| JP | H02104343 | A | 4/1990 |
| JP | 02-215451 | A | 8/1990 |
| JP | H0422351 | A | 1/1992 |
| JP | 06-197907 | A | 7/1994 |
| JP | 07-504339 | A | 5/1995 |
| JP | H07284499 | A | 10/1995 |
| JP | 08-84740 | A | 4/1996 |
| JP | 06-304178 | A | 5/1996 |
| JP | 08-131454 | A | 5/1996 |
| JP | 09-55571 | A | 2/1997 |
| JP | H10305041 | A | 11/1998 |
| JP | 10-512477 | A | 12/1998 |
| JP | 2000300559 | A | 10/2000 |
| JP | 2003510159 | A | 3/2003 |
| JP | 2004505660 | A | 2/2004 |
| JP | 2004249106 | A | 9/2004 |

(56)    References Cited

FOREIGN PATENT DOCUMENTS

| | | | |
|---|---|---|---|
| JP | 2005167058 | A | 6/2005 |
| JP | 2006511265 | A | 4/2006 |
| JP | 2007144225 | A | 6/2007 |
| JP | 2007520307 | A | 7/2007 |
| JP | 2010019554 | A | 1/2010 |
| JP | 2010029650 | A | 2/2010 |
| JP | 2010204068 | A | 9/2010 |
| JP | 2013538097 | A | 10/2013 |
| JP | 2004512502 | A | 4/2014 |
| JP | 2015002983 | A | 1/2015 |
| JP | 2015519970 | A | 7/2015 |
| JP | 2016508808 | A | 3/2016 |
| JP | 2017/506542 | A | 3/2017 |
| JP | 2017506538 | A | 3/2017 |
| JP | 2019051295 | A | 4/2019 |
| JP | 2020525167 | A | 8/2020 |
| JP | 2020525168 | A | 8/2020 |
| JP | 2020525169 | A | 8/2020 |
| JP | 6785554 | B2 | 10/2020 |
| JP | 6789944 | B2 | 11/2020 |
| JP | 2020534077 | A | 11/2020 |
| JP | 2020195788 | A | 12/2020 |
| JP | 2020535895 | A | 12/2020 |
| JP | 6832958 | B2 | 2/2021 |
| JP | 6835719 | B2 | 2/2021 |
| JP | 6838057 | B2 | 3/2021 |
| JP | 6849592 | B2 | 3/2021 |
| JP | 2021510104 | A | 4/2021 |
| JP | 6896719 | B2 | 6/2021 |
| JP | 6934933 | B2 | 9/2021 |
| JP | 6951560 | B2 | 10/2021 |
| JP | 6979633 | B2 | 12/2021 |
| JP | 6980696 | B2 | 12/2021 |
| JP | 7012726 | B2 | 1/2022 |
| JP | 2022500092 | A | 1/2022 |
| JP | 2022500093 | A | 1/2022 |
| JP | 2022501080 | A | 1/2022 |
| JP | 2022504159 | A | 1/2022 |
| JP | 2022509389 | A | 1/2022 |
| JP | 2022509391 | A | 1/2022 |
| JP | 2022509392 | A | 1/2022 |
| JP | 2022509393 | A | 1/2022 |
| JP | 2022509395 | A | 1/2022 |
| JP | 2022509401 | A | 1/2022 |
| JP | 2022509453 | A | 1/2022 |
| JP | 2022510217 | A | 1/2022 |
| JP | 7019679 | B2 | 2/2022 |
| JP | 7026118 | B2 | 2/2022 |
| JP | 2022514272 | A | 2/2022 |
| JP | 2022515488 | A | 2/2022 |
| JP | 2022516078 | A | 2/2022 |
| JP | 7053500 | B2 | 4/2022 |
| JP | 2022526104 | A | 5/2022 |
| JP | 2022527043 | A | 5/2022 |
| JP | 2022095785 | A | 6/2022 |
| JP | 7171645 | B2 | 11/2022 |
| JP | 7171663 | B2 | 11/2022 |
| JP | 7175640 | B2 | 11/2022 |
| JP | 2022546288 | A | 11/2022 |
| JP | 7187715 | B2 | 12/2022 |
| JP | 2022551875 | A | 12/2022 |
| JP | 2022552229 | A | 12/2022 |
| JP | 7201819 | B2 | 1/2023 |
| JP | 7232204 | B2 | 3/2023 |
| JP | 7239466 | B2 | 3/2023 |
| JP | 7265525 | B2 | 4/2023 |
| JP | 2023071859 | A | 5/2023 |
| JP | 7292448 | B2 | 6/2023 |
| JP | 7299992 | B2 | 6/2023 |
| JP | 7302936 | B2 | 7/2023 |
| JP | 7304344 | B2 | 7/2023 |
| JP | 7321162 | B2 | 8/2023 |
| JP | 7325430 | B2 | 8/2023 |
| JP | 7335367 | B2 | 8/2023 |
| JP | 7340594 | B2 | 9/2023 |
| JP | 7346293 | B2 | 9/2023 |
| JP | 7352561 | B2 | 9/2023 |
| JP | 7358391 | B2 | 10/2023 |
| JP | 7359765 | B2 | 10/2023 |
| JP | 7370386 | B2 | 10/2023 |
| JP | 2023162327 | A | 11/2023 |
| JP | 7391100 | B2 | 12/2023 |
| JP | 2024010135 | A | 1/2024 |
| JP | 2024020483 | A | 2/2024 |
| JP | 7479288 | B2 | 5/2024 |
| JP | 7479351 | B2 | 5/2024 |
| JP | 7485383 | B2 | 5/2024 |
| JP | 7530561 | B2 | 8/2024 |
| JP | 7542708 | B2 | 8/2024 |
| JP | 2024161427 | A | 11/2024 |
| JP | 7612816 | B2 | 1/2025 |
| JP | 7641600 | B2 | 3/2025 |
| KR | 102574559 | B1 | 9/2023 |
| KR | 102764982 | B1 | 2/2025 |
| RU | 2589649 | C1 | 7/2016 |
| WO | WO94/06355 | A1 | 3/1994 |
| WO | WO02/32506 | A1 | 4/2002 |
| WO | WO2005/018469 | A1 | 3/2005 |
| WO | WO2008/051484 | A2 | 5/2008 |
| WO | WO2011/040054 | A1 | 7/2011 |
| WO | WO2011/092683 | A1 | 8/2011 |
| WO | WO2011/154654 | A2 | 12/2011 |
| WO | WO2014/008594 | A1 | 1/2014 |
| WO | WO2014/071386 | A1 | 5/2014 |
| WO | WO2015/031532 | A1 | 3/2015 |
| WO | WO2015/000953 | A1 | 4/2015 |
| WO | WO2015/153909 | A2 | 10/2015 |
| WO | WO2016/099279 | A1 | 6/2016 |
| WO | WO2018/149671 | A1 | 8/2018 |
| WO | WO2018/208189 | A1 | 11/2018 |
| WO | WO2019/081329 | A1 | 5/2019 |
| WO | WO2019/117926 | A1 | 6/2019 |
| WO | WO2019/122941 | A1 | 6/2019 |
| WO | WO2019/148154 | A1 | 8/2019 |
| WO | WO2020/074615 | A1 | 4/2020 |
| WO | WO2020/087049 | A1 | 4/2020 |
| WO | WO2020/112688 | A1 | 6/2020 |
| WO | WO2020/217098 | A2 | 10/2020 |
| WO | WO2020/237382 | A1 | 12/2020 |
| WO | WO2020/245660 | A1 | 12/2020 |
| WO | WO2021/014221 | A1 | 1/2021 |
| WO | WO2021/032887 | A1 | 2/2021 |
| WO | WO2021/069216 | A1 | 4/2021 |
| WO | WO2021/069971 | A1 | 4/2021 |
| WO | WO2021/089810 | A1 | 5/2021 |
| WO | WO2021/105358 | A1 | 6/2021 |
| WO | WO2021/115958 | A1 | 6/2021 |
| WO | WO2021/116763 | A1 | 6/2021 |
| WO | WO2021/122253 | A1 | 6/2021 |
| WO | WO2021/123905 | A2 | 6/2021 |
| WO | WO2021/123906 | A1 | 6/2021 |
| WO | WO2021/140042 | A1 | 7/2021 |
| WO | WO2021/142090 | A1 | 7/2021 |
| WO | WO2021/170510 | A1 | 9/2021 |
| WO | WO2021/175626 | A1 | 9/2021 |
| WO | WO2021/176275 | A1 | 9/2021 |
| WO | WO2021/178961 | A1 | 9/2021 |
| WO | WO2021/180501 | A1 | 9/2021 |
| WO | WO2021/180550 | A1 | 9/2021 |
| WO | WO2021/213927 | A1 | 10/2021 |
| WO | WO2021/249936 | A1 | 12/2021 |
| WO | WO2021/258007 | A1 | 12/2021 |
| WO | WO2022/013266 | A1 | 1/2022 |
| WO | WO2022/040493 | A1 | 2/2022 |
| WO | WO2022/047193 | A8 | 3/2022 |
| WO | WO2022/056394 | A1 | 3/2022 |
| WO | WO2022/069254 | A1 | 4/2022 |
| WO | WO2022/069303 | A2 | 4/2022 |
| WO | WO2022/069327 | A2 | 4/2022 |
| WO | WO2022/078744 | A1 | 4/2022 |
| WO | WO2022/097138 | A1 | 5/2022 |
| WO | WO2022/106891 | A1 | 5/2022 |
| WO | WO2022/152724 | A1 | 7/2022 |
| WO | WO2022/152827 | A1 | 7/2022 |

(56)　　　　　References Cited

FOREIGN PATENT DOCUMENTS

| WO | WO2022/152828 A1 | 7/2022 |
| WO | WO2022/238058 A1 | 11/2022 |
| WO | WO2022/238092 A1 | 11/2022 |
| WO | WO2022/238229 A1 | 11/2022 |
| WO | WO2022/238276 A1 | 11/2022 |
| WO | WO2022/238392 A1 | 11/2022 |
| WO | WO2022/247242 A1 | 12/2022 |
| WO | WO2023/084307 A1 | 5/2023 |
| WO | WO2023/110556 A1 | 6/2023 |
| WO | WO2023/117721 A1 | 6/2023 |
| WO | WO2023/131566 A1 | 7/2023 |
| WO | WO2023/131574 A1 | 7/2023 |
| WO | WO2023/135024 A1 | 7/2023 |
| WO | WO2023/141653 A2 | 7/2023 |
| WO | WO2023/152639 A1 | 8/2023 |
| WO | WO2023/169967 A1 | 9/2023 |

OTHER PUBLICATIONS

Cain et al.; Concentric-ring and sector-vortex phased-array applicators for ultrasound hyperthermia; IEEE Transactions on Microwave Theory and Techniques; 34(5); pp. 542-551; May 1986.

Hynynen et al.; Feasibility of using ultrasound phased arrays for MRI monitored noninvasive surgery; IEEE transactions on ultrasonics, ferroelectrics, and frequency control; 43(6); pp. 1043-1053; Nov. 1996.

Cannata et al.; U.S. Appl. No. 18/594,843 entitled "Histotripsy systems and methods, " filed Mar. 4, 2024.

Cannata et al.; U.S. Appl. No. 18/630,758 entitled "Histotripsy systems and methods," filed Apr. 9, 2024.

Cannata et al.; U.S. Appl. No. 18/642,529 entitled "Histotripsy systems and associated methods including user interfaces and workflows for treatment planning and therapy," filed Apr. 22, 2024.

Maxwell et al.; U.S. Appl. No. 18/737,731 entitled "Histotripsy for thrombolysis," filed Jun. 7, 2024.

Cannata et al.; U.S. Appl. No. 18/737,746 entitled "Histotripsy excitation sequences optimized for bubble cloud formation using shoock scattering," filed Jun. 7, 2024.

Stopek.; U.S. Appl. No. 18/761,937 entitled "Minimally invasive histotripsy systems and methods," filed Jul. 2, 2024.

Kisting et al.; Imaging for targeting, monitoring, and assessment after histotripsy: a non-invasive, non-thermal therapy for cancer; Blood Vessels; vol. 10; pp. 15-21; Mar. 2023.

Lu et al.; Transcranial MR-guided histotripsy system; IEEE transactions on ultrasonics, ferroelectrics, and frequency control; 66(9); pp. 2917-2929; Mar. 23, 2021.

Rosnitskiy et al.; Method for designing multielement fully populated random phased arrays for ultrasound surgery applications. IEEE transactions on ultrasonics, ferroelectrics, and frequency control; 65(4); pp. 630-637; Jan. 31, 2018.

Stocker et al.; Endocavity histotripsy for efficient tissue ablationRtransducer design and characterization. IEEE transactions on ultrasonics, ferroelectrics, and frequency control; 68(9); pp. 2896-2905; Jan. 28, 2021.

Wijlemans et al.; Magnetic resonance-guided high-intensity focused ultrasound (MR-HIFU) ablation of liver tumours; Cancer Imaging; 12(2); pp. 387-394; Sep. 28, 2012.

Woodacre et al.; A low-cost miniature histotripsy transducer for precision tissue ablation. IEEE transactions on ultrasonics, ferroelectrics, and frequency control; 65(11); pp. 2131-2140; Nov. 1, 2018.

Miller et al.; U.S. Appl. No. 18/924,812 entitled "Histotripsy systems and methods," filed Oct. 23, 2024.

International Society for Magnetic Resonance in Medicine (ISMRM); No. 105; XP040714022;I Jul. 24, 2020.

Hoogenboom et al.; Mechanical high-intensity focused ultrasound destruction of soft tissue: working mechanisms and physiologic effects; Ultrasound in medicine & biology; 41(6); pp. 1500-1517; Jun. 1, 2015.

Ma et al.; Acoustic focusing and imaging via phononic crystal and acoustic metamaterials; Journal of Applied Physics; 131(1); doi:10.10653/5.0074503; 29 pages; Jan. 5, 2022.

Sukovich et al.; Real-time transcranial histotripsy treatment localization and mapping using acoustic cavitation emission feedback; IEEE transactions on ultrasonics, ferroelectrics, and frequency control; 67(6); pp. 1178-1791; Jan. 17, 2020.

Shaffer et al.; U.S. Appl. No. 18/832,708 entitled "Histotripsy systems and methods," filed Jul. 24, 2024.

Snell et al.; U.S. Appl. No. 18/886,807 entitled "Simulation software and tools for evaluating histotripsu therapy for a given pose and position of a therapy array," filed Sep. 16, 2024.

Schell et al.; U.S. Appl. No. 18/890,580 entitled "Co-registration techniques between computed tomography imaging systems and histrotripsy robotic systems," filed Nov. 14, 2024.

Cannata et al.; U.S. Appl. No. 18/812,761 entitled "Histotripsy systems and methods," filed Aug. 22, 2024.

Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.

Appel et al.; Stereoscopic highspeed recording of bubble filaments; Ultrasonics Sonochemistry; vol. 11(1); pp. 39-42; Jan. 2004.

Arani et al.; Transurethral prostate magnetic resonance elestography; prospective imaging requirements; Magn. Reson. Med.; 65(2); pp. 340-349; Feb. 2011.

Aschoff et al.; How does alteration of hepatic blood flow affect liver perfusion and radiofrequency-induced thermal lesion size in rabbit liver ?; J Magn Reson Imaging; 13(1); pp. 57-63; Jan. 2001.

Atchley et al.; Thresholds for cavitation produced in water by pulsed ultrasound; Ultrasonics.; vol. 26(5); pp. 280-285; Sep. 1988.

Avago Technologies; ACNV2601 High Insulation Voltage 10 MBd Digital Opotcoupler. Avago Technologies Data Sheet; pp. 1-11; Jul. 29, 2010.

Avago Technologies; Avago's ACNV2601 optocoupler is an optically coupled logic gate; Data Sheet; 2 pages; Jul. 29, 2010.

Avtech; AVR-8 Data sheet; May 23, 2004; 3 pages; retrieved from the internet (http//www.avtechpulse.com).

Bak; Rapid protytyping or rapid production? 3D printing processes move industry towards the latter; Assembly Automation; 23(4); pp. 340-345; Dec. 1, 2003.

Billson et al.; Rapid prototyping technologies for ultrasonic beam focussing in NDE; IEEE International Ultrasonic Symposium Proceedings; pp. 2472-2474; Oct. 2011.

Bjoerk et al.; Cool/MOS CP—How to make most beneficial use of the generation of super junction technology devices. Infineon Technologies AG. [retrieved Feb. 4, 2014] from the internet (http://www.infineon.com/dgdl/infineon+-+Application+Note+-+PowerMOSFETs+-+600V+CoolMOS%E284%A2+-+CP+Most+beneficial+use+of+superjunction+technologie+devices.pdf?folderid=db3a304412b407950112b408e8c90004&fileId=db3a304412b407950112b40ac9a40688>pages1, 4, 14; Feb. 2007.

Bland et al.; Surgical Oncology; McGraw Hill; Chap. 5 (Cavitron Ultrasonic Aspirator); pp. 461-462; Jan. 29, 2001.

Burdin et al.; Implementation of the laser diffraction technique for cavitation bubble investigations; Particle & Particle Systems Characterization; vol. 19; pp. 73-83; May 2002.

Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.

Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).

Chan et al.; An image-guided high intensity focused ultrasound device for uterine fibroids treatment; Medical Physics, vol. 29, pp. 2611-2620, Nov. 2002.

Clasen et al.; MR-guided radiofrequency ablation of hepatocellular carcinoma: Long-term effectiveness; J Vase Interv Radiol; 22(6); pp. 762-770; Jun. 2011.

(56) References Cited

OTHER PUBLICATIONS

Clement et al.; A hemisphere array for non-invasive ultrasound brain therapy and surgery; Physics in Medicine and Biology, vol. 45, p. 3707-3719, Dec. 2000.

Cline et al.; Magnetic resonance-guided thermal surgery; Magnetic Resonance in Medicine; 30(1); pp. 98-106; Jul. 1993.

Curiel et al.; Elastography for the follow-up of high-intensity focused ultrasound prostate cancer treatment: Initial comparison with MRI; Ultrasound Med. Biol; 31(11); pp. 1461-1468; Nov. 2005.

Desilets et al.; The Design of Efficient Broad-Band Piezoelectric Transducers; Sonics and Ultrasonics, IEEE Transactions on, vol. 25, pp. 115-125, May 1978.

Dovedi et al.; Acquired Resistance to Fractionated Radiotherapy Can Be Overcome by Concurrent PD-LI Blockade; Cancer Research; 74(19); pp. 5458-5468; Oct. 1, 2014.

Emelianov et al.; Triplex ultrasound: Elasticity imaging to age deep venous thrombosis; Ultrasound Med Biol; 28(6); pp. 757-767; Jun. 2002.

Gateau et al.; Transcranial ultrasonic therapy based on time reversal of acoustically induced cavitation bubble signature. IEEE Transactions on Biomedical Engineering; 57(1); pp. 134-144; Sep. 18, 2009.

Giannatsis et al.; Additive fabrication technologies applied to medicine and health care: a review; The International Journal of Advanced Manufacturing Technology; 40(1-2); pp. 116-127; Jan. 2009.

Gudra et al.; Influence of acoustic impedance of multilayer acoustic systems on the transfer function of ultrasonic airborne transducers; Ultrasonics, vol. 40, pp. 457-463, May 2002.

Hall et al.; A Low Cost Compact 512 Channel Therapeutic Ultrasound System for Transcutaneous Ultrasound Surgery; AIP Conference Proceedings, Boston, MA; vol. 829, pp. 445-449, Oct. 27-29, 2005.

Hall et al.; Acoustic Access to the Prostate for Extracorporeal Ultrasound Ablation; Journal of Endourology, vol. 24, pp. 1875-1881, Nov. 2010.

Hall et al.; Histotripsy of the prostate: dose effects in a chronic canine model; Urology; 74(4); pp. 932-937; Oct. 2009 (author manuscript).

Hall et al.; Imaging feedback of tissue liquefaction (histotripsy) in ultrasound surgery; IEEE Ultrasonic Symposium, Sep. 18-21, 2005, pp. 1732-1734.

Haller et al.; Determination of acoustic cavitation probabilities and thresholds using a single focusing transducer to induce and detect acoustic cavitation events: 1. Method and terminology; Ultrasound in Medicine & Biology; 44(2); pp. 377-396; Feb. 1, 2018.

Hartmann; Ultrasonic properties of poly(4-methyl pentene-1), Journal of Applied Physics, vol. 51, pp. 310-314, Jan. 1980.

Hobarth et al.; Color flow doppler sonography for extracorporal shock wave lithotripsy; Journal of Urology; 150(6); pp. 1768-1770; Dec. 1, 1993.

Holland et al.; Thresholds for transient cavitation produced by pulsed ultrasound in a controlled nuclei environment; J. Acoust. Soc. Am .; vol. 88(5); pp. 2059-2069; Nov. 1990.

Huber et al.; Influence of shock wave pressure amplitude and pulse repetition frequency on the lifespan, size and number of transient cavities in the field of an electromagnetic lithotripter; Physics in Medicine and Biology; vol. 43 (10); pp. 3113-3128; Oct. 1998.

Hynynen et al.; Tissue thermometry during ultrasound exposure; European Urology; 23(Suppl 1); pp. 12-16; (the year of publication is sufficiently earlier than the effective U.S. filing date and any foreign priority date so that the particular month of publication is not in issue) 1993.

Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.

Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.

Kim et al.; Dependence of particle volume fraction on sound velocity and attenuation of EPDM composites; Ultrasonics, vol. 46, pp. 177-183, Feb. 2007.

Kim et al.; Development of a wearable robotic positioning system for noninvasive transcranial focused ultrasound stimulation. IEEE/ASME Transactions on Mechatronics; 21(5); pp. 2284-2293; Jun. 13, 2016.

Konofagou; Quo vadis elasticity imaging ?; Ultrasonics; 42(1-9); pp. 331-336; Apr. 2004.

Krimholtz et al.; New equivalent circuits for elementary piezoelectric transducers; Electronics Letters, vol. 6, pp. 398-399, Jun. 1970.

Kruse et al.; Tissue characterization using magnetic resonance elastography: Preliminary results; Phys. Med. Biol; 45(6); pp. 1579-1590; Jun. 2000.

Lake et al.; Histotripsy: minimally invasive technology for prostatic tissue ablation in an in vivo canine model; Urology; 72(3); pp. 682-686; Sep. 2008.

Lauterborn et al.; Cavitation bubble dynamics studied by high speed photography and holography: part one; Ultrasonics; vol. 23; pp. 260-268; Nov. 1985.

Lensing et al.; Deep-vein thrombosis; The Lancet, vol. 353, pp. 479-485, Feb. 6, 1999.

Lin et al.; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).

Liu et al.; Real-time 2-D temperature imaging using ultrasound; IEEE Trans Biomed Eng; 57(1); pp. 12-16; Jan. 2010 (author manuscript, 16 pgs.).

Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).

Macoskey; Acoustic methods for histotripsy feedback; (Dissertation); Biomedical Engineering and Science Computing; University of Michigan 2019; 207 pages; retrived from the internet (https://deepblue.lib.umich.edu/handle/2027.42/149,988) on Feb. 2022.

Manes et al.; Design of a Simplified Delay System for Ultrasound Phased Array Imaging; Sonics and Ultrasonics, IEEE Transactions on, vol. 30, pp. 350-354, Nov. 1983.

Maréchal et al.; Effect of Radial Displacement of Lens on Response of Focused Ultrasonic Transducer; Japanese Journal of Applied Physics, vol. 46, p. 3077-3085; May 15, 2007.

Maréchal et al.; Lens-focused transducer modeling using an extended KLM model; Ultrasonics, vol. 46, pp. 155-167, May 2007.

Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.

Maxwell et al.; Cavitation clouds created by shock scattering from bubbles during histotripsy; J. Acoust. Soc. Am.; 130(4); pp. 1888-1898; Oct. 2011.

Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).

Maxwell; Noninvasive thrombolysis using histotripsy pulsed ultrasound cavitation therapy; PhD Dissertation. University of Michigan, Ann Arbor, Michigan. Jun. 2012.

Maxwell et al.; In-vivo study of non-invasive thrombolysis by histotripsy in a porcine model; IEEE international Ultrasonics Symposium; IEEE; p. 220-223; Sep. 20, 2009.

Maxwell et al.; The role of compressional pressure in the formation of dense bubble clouds in histotripsy; 2009 IEEE International Ultrasonics Symposium; pp. 81-84; Sep. 20, 2009.

Miller et al.; A review of in vitro bioeffects of inertial ultrasonic cavitation from a mechanistic perspective; Ultrasound in Medicine and Biology: vol. 22; pp. 1131-1154; (the year of publication is sufficiently earlier than the effective U.S. filing date and any foreign priority date so that the particular month of publication is not in issue) 1996.

Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.

(56) References Cited

OTHER PUBLICATIONS

Miller et al.; Real-time elastography-based monitoring of histotripsy tissue fractionation using color doppler; Ultrasonics Symposium (IUS); 2012 IEEE International, 8 pages; Oct. 7-10, 2012.

Nightingale et al.; Analysis of contrast in images generated with transient acoustic radiation force; Ultrasound Med Biol; 32(1); pp. 61-72; Jan. 2006.

Ohl et al.; Bubble dynamics, shock waves and sonoluminescence; Phil. Trans. R. Soc. Lond. A; vol. 357; pp. 269-294; (the year of publication is sufficiently earlier than the effective U.S. filing date and any foreign priority date so that the particular month of publication is not in issue) 1999.

Okada et al.; A case of hepatocellular carcinoma treated by MR-guided focused ultrasound ablation with respiratory gating; Magn Reson Med Sci; 5(3); pp. 167-171; Oct. 2006.

Palmeri et al.; Acoustic radiation force-based elasticity imaging methods; Interface Focus; 1; pp. 553-564; Aug. 2011.

Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.

Parsons et al.; Pulsed cavitational ultrasound therapy for controlled tissue homogenization; Ultrasound in Med. & Biol.; vol. 32(1); pp. 115-129; Jan. 2006.

Pishchalnikov et al.; Cavitation Bubble Cluster Activity in the Breakage of Kidney Stones by Lithotripter Shock Waves; J Endourol.; 17(7): 435-446; Sep. 2003.

Porter et al.; Reduction in left ventricular cavitary attenuation and improvement in posterior myocardial contrast . . . ; J Am Soc Echocardiography; pp. 437-441; Jul.-Aug. 1996.

Qu et al.; Non-thermal histotripsy tumor ablation promotes abscopal immune responses that enhance cancer immunotherapy; Journal for immunotherapy of cancer; 8(1); Jan. 15, 2020.

Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.

Rosenschein et al.; Ultrasound Imaging-Guided Noninvasive Ultrasound Thrombolysis: Preclinical Results; Circulation; vol. 102; pp. 238-245, Jul. 11, 2000.

Rowland et al.; MRI study of hepatic tumours following high intensity focused ultrasound surgery; British Journal of Radiology; 70; pp. 144-153; Feb. 1997.

Roy et al.; A precise technique for the measurement of acoustic cavitation thresholds and some preliminary results; Journal of the Acoustical Society of America; vol. 78(5); pp. 1799-1805; Nov. 1985.

Sapareto et al.; Thermal dose determination in cancer therapy; Int J Radiat Oncol Biol Phys; 10(6); pp. 787-800; Apr. 1984.

Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.

Sato et al.; Experimental Investigation of Phased Array Using Tapered Matching Layers. 2002 IEEE Ultrasound Symposium. vol. 2; pp. 1235-1238, Oct. 2002.

Sferruzza et al.; Generation of high power unipolar pulse with a piezocomposite transducer; In 1999 IEEE Ultrasonics Symposium Proceedings; International Symposium (Cat. No. 99CH37027); vol. 2; pp. 1125-1128; Oct. 17, 1999.

Shung; Diagnostic Ultrasound: Imaging and Blood Flow Measurements; Taylor and Francis Group, LLC; Boca Raton, FL; 207 pages; (the year of publication is sufficiently earlier than the effective U.S. filing date and any foreign priority date so that the particular month of publication is not in issue) 2006.

Simonin et al.; Characterization of heterogeneous structure in a polymer object manufactured by stereolithography with low-frequency microechography; Journal of Materials Chemistry; vol. 6, pp. 1595-1599, Sep. 1996.

Sokolov et al.; Use of a dual-pulse lithotripter to generate a localized and intensified cavitation field; Journal of the Acoustical Society of America; vol. 110(3); pp. 1685-1695; Sep. 2001.

Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).

Souchon et al.; Visualisation of HIFU lesions using elastography of the human prostate in vivo: Preliminary results; Ultrasound Med. Biol; 29(7); pp. 1007-1015; Jul. 2003.

Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.

Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011 [retrieved on Jan. 28, 2014] from: (http://web archive.org/web/20110720091822/http://www.histotripsy.umich.edu/index.html> entiredocument) Jul. 2011.

Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.

Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.

Van Kervel et al.; A calculation scheme for the optimum design of ultrasonic transducers; Ultrasonics, vol. 21, pp. 134-140, May 1983.

Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.

Wikipedia; Medical ultrasound; 15 pages; retrieved from the internet (https://en.wikipedia.org/w/index.php?title=Medical_utrasound&oldid=515340960) on Jan. 12, 2018.

Wu et al.; Mechanism and dynamics of hydrodynamic-acoustic cavitation (HAC); Ultrasonics sonochemistry; vol. 49., pp. 89-96; Dec. 1, 2018.

Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).

Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.

Xu et al.; Controlled ultrasound tissue erosion: the role of dynamic interaction between insonation and microbubble activity; Journal of the Acoustical Society of America; vol. 117(1); pp. 424-435; Jan. 2005.

Xu et al.; Controlled ultrasound tissue erosion; IEEE Transaction on Ultrasonics, Ferroelectrics, and Frequency Control; vol. 51 (6); pp. 726-736; Jun. 2004.

Xu et al.; Effects of acoustic parameters on bubble cloud dynamics in ultrasound tissue erosion (histotripsy); Journal of the Acoustical Society of America; vol. 122(1); pp. 229-236; Jul. 2007.

Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; pp. 2091R2101; Oct. 2007.

Xu et al.; Investigation of intensity threshold for ultrasound tissue erosion; Ultrasound in Med. & Biol.; vol. 31(12); pp. 1673-1682; Dec. 2005.

Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.

Yan et al.; A review of rapid prototyping technologies and systems; Computer-Aided Design, vol. 28, pp. 307-318, Apr. 1996.

Zhang et al.; A fast tissue stiffness-dependent elastography for HIFU-induced lesions inspection; Ultrasonics; 51(8); pp. 857-869; Dec. 2011.

(56)     References Cited

OTHER PUBLICATIONS

Zheng et al.; An acoustic backscatter-based method for localization of lesions induced by high-intensity focused ultrasound; Ultrasound Med Biol; 36(4); pp. 610-622; Apr. 2010.

Cannata et al.; U.S. Appl. No. 18/311,050 entitled "Histotripsy systems and methods," filed May 2, 2023.

Maxwell et al.; U.S. Appl. No. 18/329,459 entitled "Histotripsy for thrombolysis," filed Jun. 5, 2023.

Duryea et al.; U.S. Appl. No. 18/497,856 entitled "Histotripsy systems and methods," filed Oct. 31, 2023.

Duryea et al.; U.S. Appl. No. 18/498,966 entitled "Histotripsy systems and methods," filed Oct. 31, 2023.

Duryea et al.; U.S. Appl. No. 18/498,979 entitled "Histotripsy systems and methods," filed Oct. 31, 2023.

Xu et al.; U.S. Appl. No. 18/555,683 entitled "Design and fabrication of therapeutic ultrasound transducer with arbitrarily shaped, densely packing, removable modular elements," filed Oct. 16, 2023.

Miller et al.; U.S. Appl. No. 18/499,847 entitled "Histotripsy systems and methods," filed Nov. 1, 2023.

Xu et al.; U.S. Appl. No. 18/568,038 entitled "Minimally invasive histotripsy systems and methods," filed Dec. 7, 2023.

Bogott et al.; U.S. Appl. No. 18/535,728 entitled "Fluidics cart and degassing system for histotripsy systems and methods," filed Dec. 11, 2023.

Grumbir et al.; U.S. Appl. No. 18/535,877 entitled "Ultrasound coupling device for histotripsy systems and methods," filed Dec. 11, 2023.

* cited by examiner replicated each channel

Identify target tissue
402

Apply histotripsy therapy to the target tissue with an all-in-one
ultrasound system
404

Select a different ultrasound modality in all-in-one ultrasound system
406

Apply different ultrasound modality to target tissue with the all-in-one
ultrasound system
408

ALL-IN-ONE ULTRASOUND SYSTEMS AND METHODS INCLUDING HISTOTRIPSY

PRIORITY CLAIM

This patent application claims priority to U.S. provisional patent application No. 63/197,919, titled "ALL-IN-ONE ULTRASOUND SYSTEMS AND METHODS INCLUDING HISTOTRIPSY" and filed on Jun. 7, 2021, which is herein incorporated by reference in its entirety.

STATEMENT AS TO FEDERALLY SPONSORED RESEARCH

This invention was made with government support under EB028309 and NS108042 awarded by the National Institutes of Health. The government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure details novel histotripsy systems configured to produce acoustic cavitation, methods, devices and procedures for the minimally and non-invasive treatment of healthy, diseased and/or injured tissue. The histotripsy systems and methods described herein, also referred to as Histotripsy, may include transducers, drive electronics, positioning robotics, imaging systems, and integrated treatment planning and control software to provide comprehensive treatment and therapy for soft tissues in a patient.

BACKGROUND

Many medical conditions require invasive surgical interventions. Invasive procedures often involve incisions, trauma to muscles, nerves and tissues, bleeding, scarring, trauma to organs, pain, need for narcotics during and following procedures, hospital stays, and risks of infection. Non-invasive and minimally invasive procedures are often favored, if available, to avoid or reduce such issues. Unfortunately, non-invasive and minimally invasive procedures may lack the precision, efficacy or safety required for treatment of many types of diseases and conditions. Enhanced non-invasive and minimally invasive procedures are needed, preferably not requiring ionizing or thermal energy for therapeutic effect.

Histotripsy, or pulsed ultrasound cavitation therapy, is a technology where extremely short, intense bursts of acoustic energy induce controlled cavitation (microbubble formation) within the focal volume. The vigorous expansion and collapse of these microbubbles mechanically homogenizes cells and tissue structures within the focal volume. This is a very different end result than the coagulative necrosis characteristic of thermal ablation. To operate within a non-thermal, Histotripsy realm; it is necessary to deliver acoustic energy in the form of high amplitude acoustic pulses with low duty cycle.

High intensity focused ultrasound (HIFU) delivers high intensity continuous ultrasound wave or long pulses from outside the body and focus to the target tissue inside the body to heat up the target tissue, resulting in thermal necrosis. The temperature increase generated by HIFU can be monitored by magnetic resonant imaging (MRI) thermometry during treatment. HIFU thermal ablation has been used clinically for treatment of benign and metastatic tumors, including tumor in pancreas, liver, prostate, breast, uterine fibroids, and essential tremor.

Hyperthermia therapy (HT) can use ultrasound to induce low heating using continuous wave or ultrasound bursts at a high duty cycle (>10%). Hyperthermia is useful to induce low temperature increase (to ~40-45 deg. C.). Hyperthermia has been shown potentially to enhance radiation therapy. Hyperthermia can be visualized with MRI thermometry, thus has been used for targeting in MR-guide ultrasound treatment.

Ultrasound can also be used to aid with drug delivery. Low intensity ultrasound combined with microbubbles has been shown to generate cavitation in the blood vessels within target zones to open up the tight junction of the blood vessel to facilitate local drug delivery. In the brain, low intensity ultrasound combined with microbubbles has been shown to open up the blood brain barrier (BBB) temporarily to allow drug delivery into the brain. Microbubble-mediated ultrasound drug delivery has been investigated to treat many diseases, including various tumors, Parkinson's disease, Alzheimer's disease, etc.

HIFU and histotripsy have both shown the potential to stimulate immune response in the brain in mouse tumor models. Microbubble-mediated ultrasound drug delivery has also been used to deliver immune drugs in pre-clinical studies. Thus, HIFU, histotripsy, microbubble-mediated ultrasound drug delivery, or hyperthermia parameters may also be used to enhance immune therapy.

Sonodynamic therapy (SDT) has been broadly defined as a synergistic effect of low energy sonication applied in combination with substances referred to as "sonosensitizers". Sonodynamic therapy can be used for drug delivery.

Low intensity focused ultrasound has shown neuromodulation effects on corticospinal and thalamocortical pathways related to movement, visual and cognitive processing, and brain connectivity related to mood change.

Compared with conventional focused ultrasound technologies, Histotripsy has important advantages: 1) the destructive process at the focus is mechanical, not thermal; 2) cavitation appears bright on ultrasound imaging thereby confirming correct targeting and localization of treatment; 3) treated tissue generally, but not always, appears darker (more hypoechoic) on ultrasound imaging, so that the operator knows what has been treated; and 4) Histotripsy produces lesions in a controlled and precise manner. It is important to emphasize that unlike thermal ablative technologies such as microwave, radiofrequency, and high-intensity focused ultrasound (HIFU), Histotripsy relies on the mechanical action of cavitation for tissue destruction. However, histotripsy therapy in combination with other ultrasound treatments opens the door for new and exciting combination treatments.

BRIEF DESCRIPTION OF THE DRAWINGS

The novel features of the invention are set forth with particularity in the claims that follow. A better understanding of the features and advantages of the present invention will be obtained by reference to the following detailed descrip-

Figure 1A:
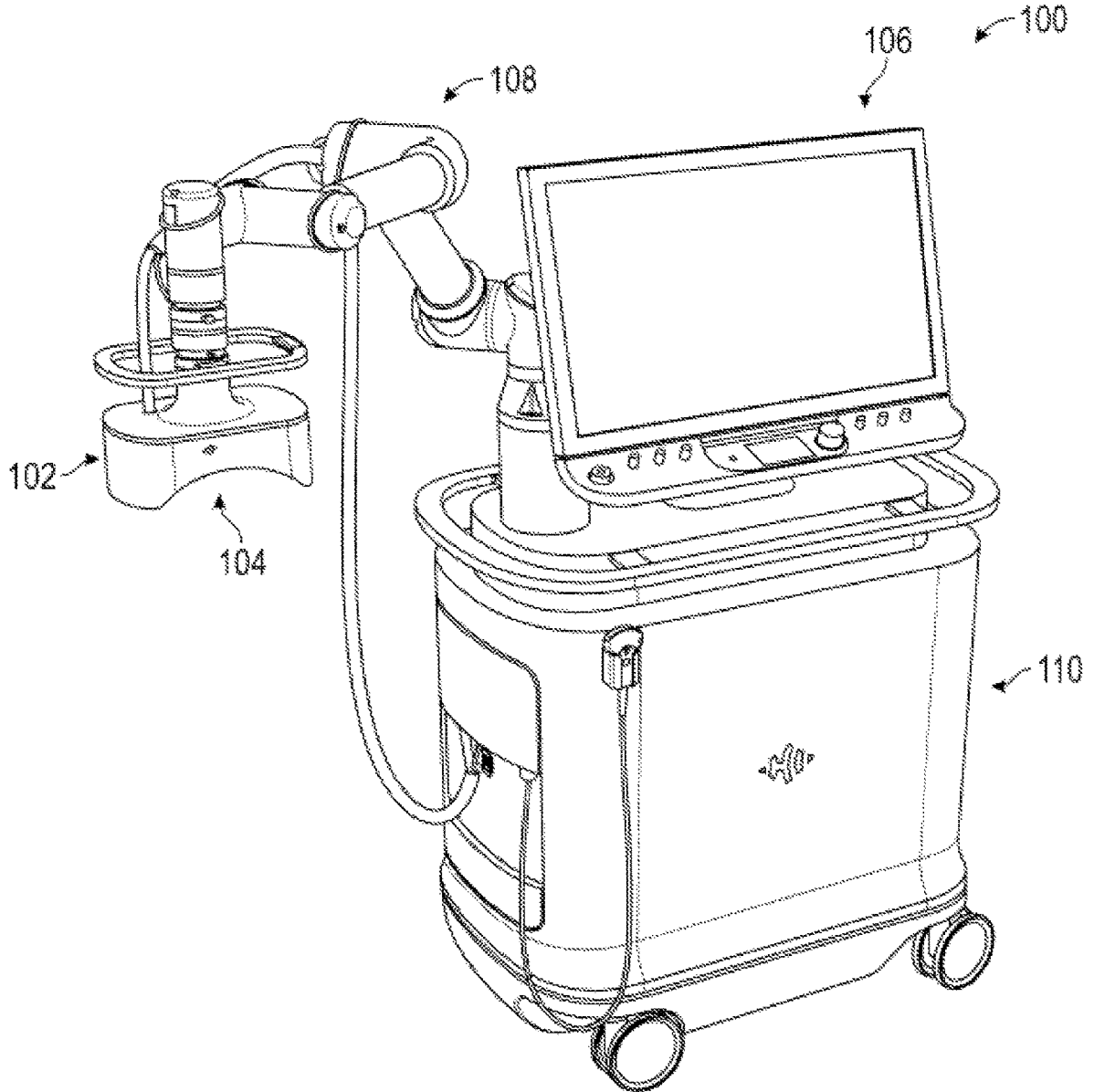
Figure 1B:
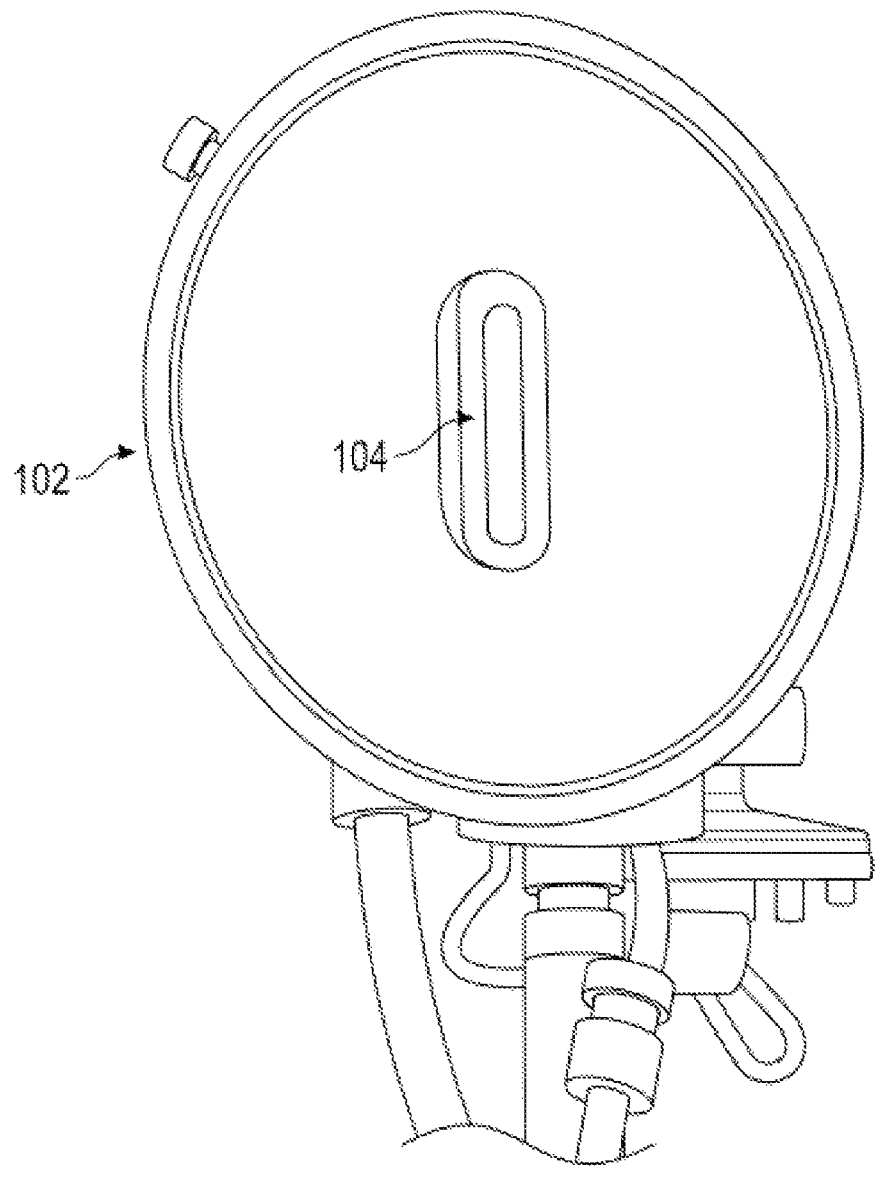

3 tion that sets forth illustrative embodiments, in which the principles of the invention are utilized, and the accompanying drawings of which:

FIGS. 1A-1B illustrate an ultrasound imaging and therapy system.

Figure 2A:
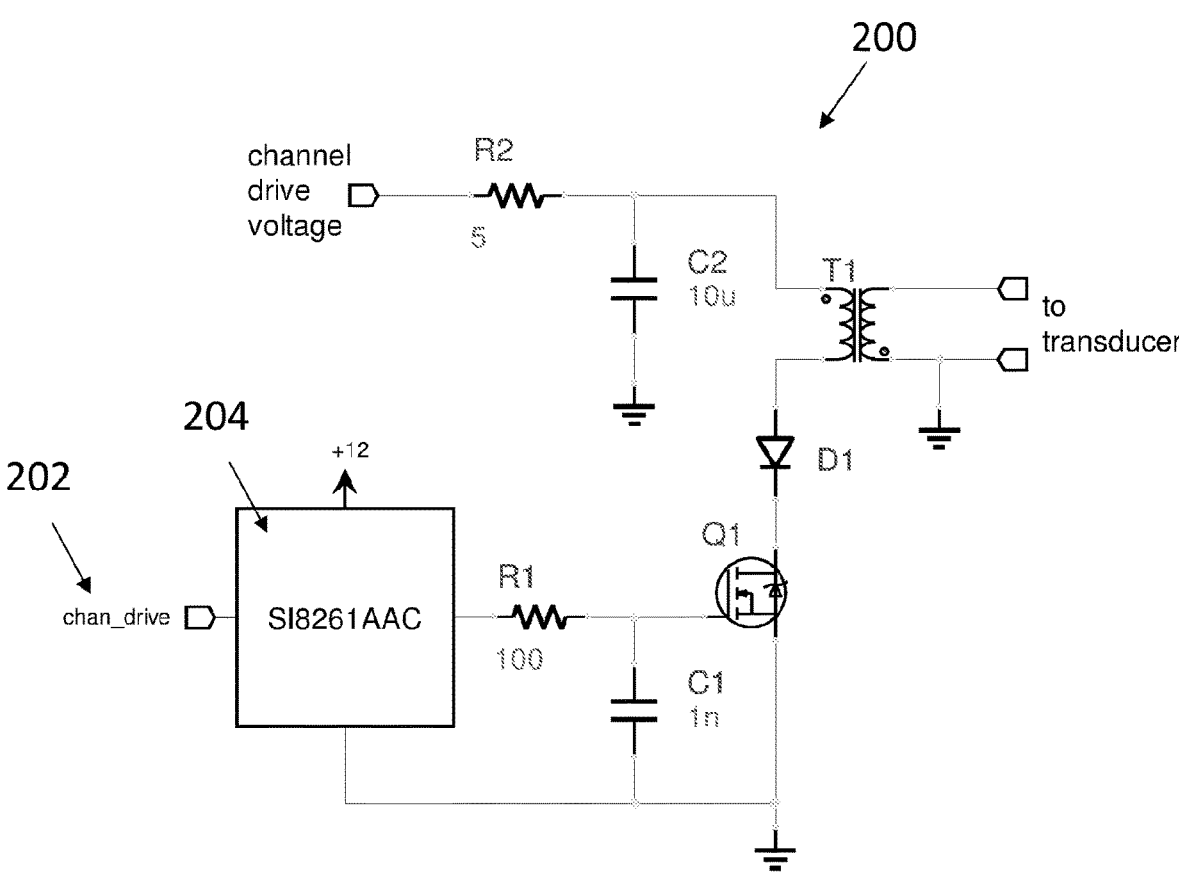

FIG. 2A is a schematic illustration of transmit drive electronics for an all-in-one ultrasound system.

Figure 2B:
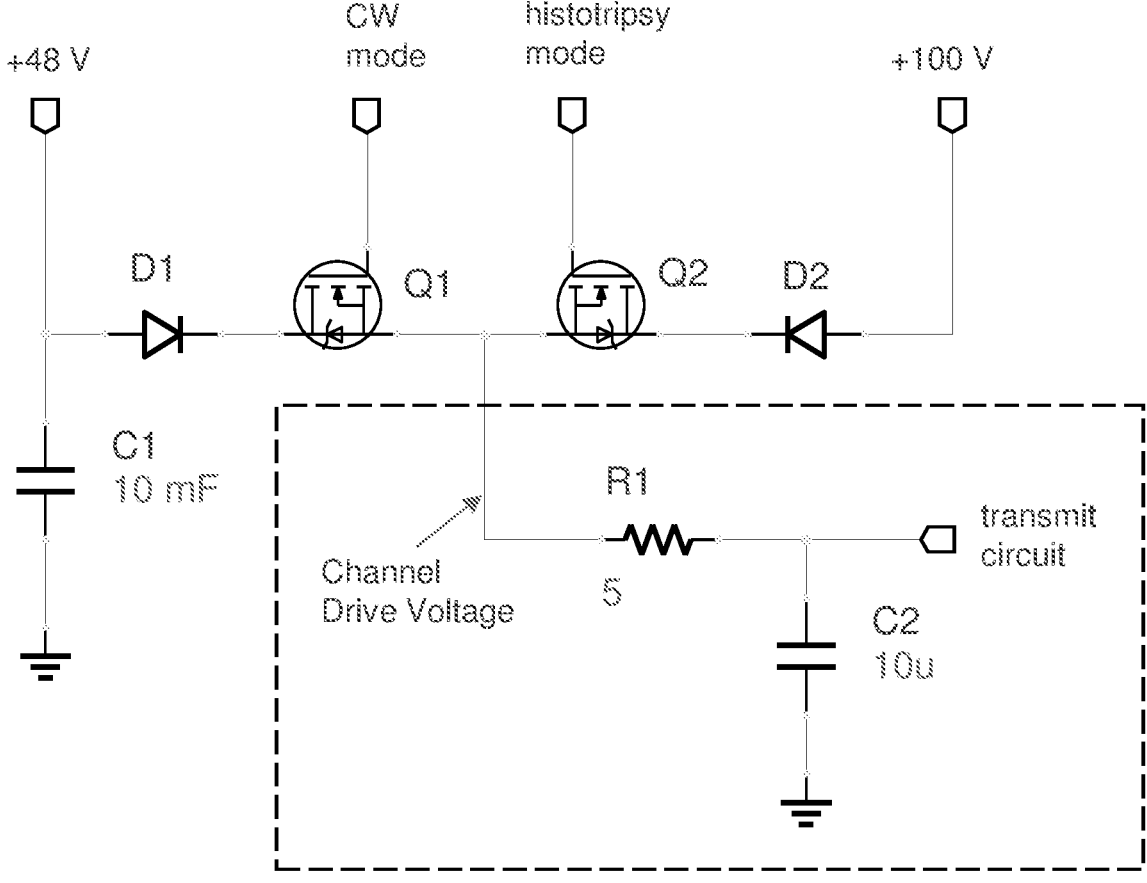
Figure 3:
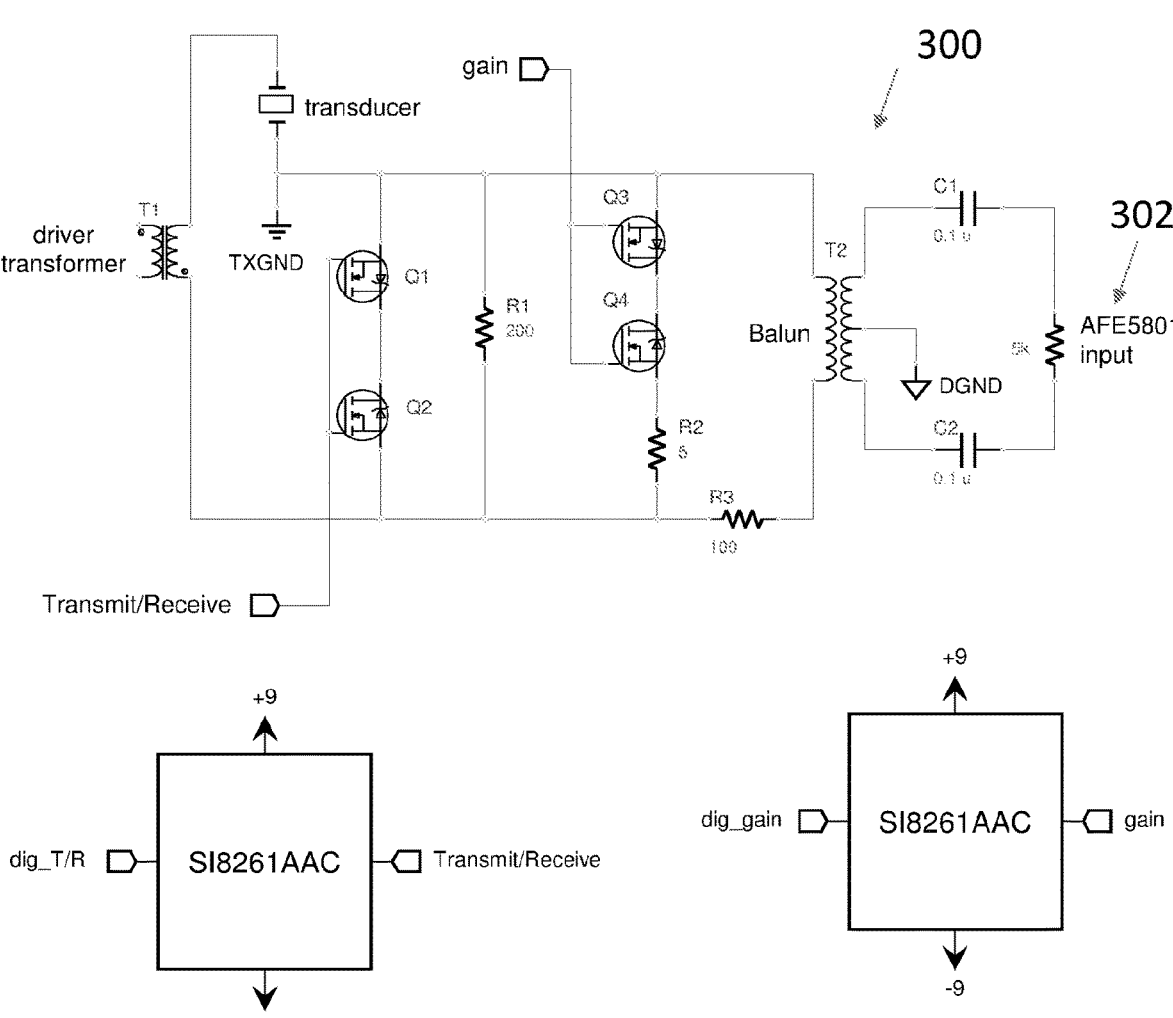

FIG. 2B is a schematic illustration of a power supply switching circuit for an all-in-one ultrasound system FIG. 3 is a schematic illustration of receive drive electronics for an all-in-one ultrasound system.

Figure 4:
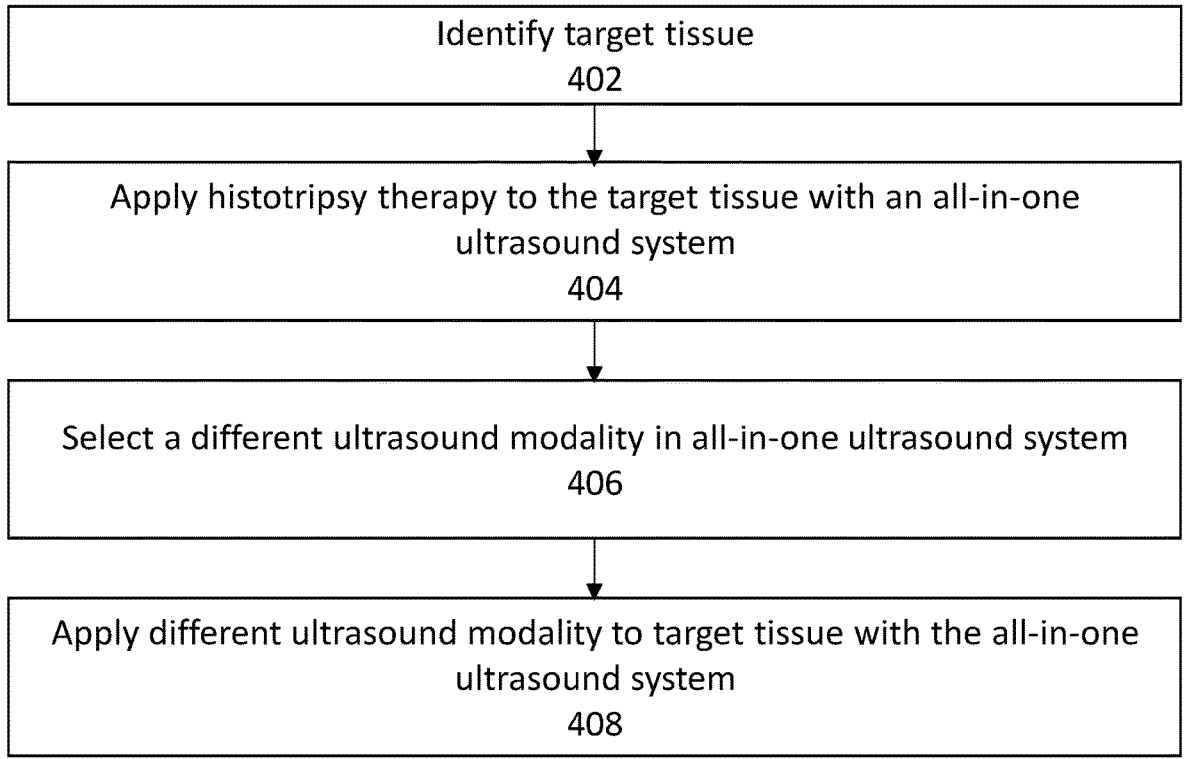

FIG. 4 is a flowchart describing a method of treating tissue.

SUMMARY OF THE DISCLOSURE

Histotripsy produces tissue fractionation through dense energetic bubble clouds generated by short, high-pressure, ultrasound pulses. When using pulses shorter than 2 cycles, the generation of these energetic bubble clouds only depends on where the peak negative pressure (P−) exceeds an intrinsic threshold for inducing cavitation in a medium (typically 26-30 MPa in soft tissue with high water content).

A method of delivering therapy to a target tissue, comprising the steps of providing an all-in-one ultrasound therapy system configured to provide a plurality of ultrasound therapy modalities to the target tissue, the all-in-one therapy system including a current driver and an ultrasound transducer array, positioning a therapy focus of the ultrasound transducer array on the target tissue, transmitting ultrasound therapy pulses of a first ultrasound therapy modality into the target tissue with a current driver and the ultrasound transducer array, selecting a second ultrasound therapy modality in the all-in-one ultrasound system, and transmitting ultrasound therapy pulses of the second ultrasound therapy modality into the target tissue with the current driver and the ultrasound transducer array.

In some embodiments, the first ultrasound therapy modality comprises histotripsy therapy. In other embodiments, the second ultrasound therapy modality is selected from the group consisting of hyperthermia/radio-sensitization, HIFU, microbubble-enhanced drug delivery, immunotherapy, sonodynamic therapy, and neuromodulation.

In one implementation, transmitting ultrasound therapy pulses further comprises turning on a transistor of the current driver to pull current through a primary winding of a transformer of the current driver, and turning off the transistor of the current driver to force the current to a secondary winding of the transformer and to the ultrasound transducer array.

In some embodiments, the secondary winding is configured to resonate with a capacitance of the ultrasound transducer array.

In one embodiment, transmitting ultrasound therapy pulses of the first ultrasound therapy modality further comprises coupling the current driver to a power supply switching circuit operating in a first operating mode, and wherein transmitting ultrasound therapy pulses of the second ultrasound therapy modality further comprises coupling the current driver to the power supply switching circuit operating in a second operating mode.

Also provided is an ultrasound system driving architecture configured to drive an ultrasound transducer array with a plurality of ultrasound modalities, the ultrasound system driving architecture comprising a power supply switching circuit configured to switch between a first power mode that provides a first voltage and a first current and a second power mode that provides a second voltage and a second current, wherein the second voltage is higher than the first voltage and the second current is lower than the first current, and a current driver circuit comprising a gate driver configured to receive a digital drive signal, a transformer electrically coupled to the ultrasound transducer array, and a transistor electrically coupled to the gate driver and the transformer, wherein the gate driver is configured to drive the transistor at a first pulse repetition frequency when the power supply switching circuit is operating in the first power mode to produce ultrasound pulses of a first ultrasound therapy modality, and wherein the gate driver is configured to drive the transistor at a second pulse repetition frequency when the power supply switching circuit is operating in the second power mode to produce ultrasound pulses of a second ultrasound therapy modality.

In one embodiment, the first ultrasound therapy modality is selected from the group consisting of hyperthermia/radio-sensitization, HIFU, microbubble-enhanced drug delivery, immunotherapy, sonodynamic therapy, and neuromodulation.

In another embodiment, the second ultrasound therapy modality comprises histotripsy.

In some embodiments, the ultrasound driving system architecture further comprises a first resistor and a first capacitor electrically coupled to the transistor and configured to slow down a turn-on and a turn off time of the transistor to reduce RF noise emissions.

In other embodiments, the ultrasound driving system architecture further comprises a blocking diode electrically connected to the transistor and configured to prevent the transistor from conducting when a polarity of the transistor is negative.

In some examples, a secondary winding of the transformer is configured to resonate with a capacitance of the ultrasound transducer array.

In some embodiments, the power supply switching circuit further comprises a first transistor configured to connect the power supply switching circuit to a first power supply, and a second transistor configured to connect the power supply switching circuit to a second power supply.

In some embodiments, the current driver circuit is further configured to enable the ultrasound transducer array to measure ultrasound signals.

In one example, the current driver circuit further comprises a current sensing resistor and a digitizer configured to measure a voltage across the current sensing resistor.

In some embodiments, the ultrasound driving system architecture further comprises a pair of MOSFETs in parallel with the current sensing resistor configured to block transmit currents.

In other embodiments, the ultrasound driving system architecture further comprises a second current sensing resistor configured to be switched into the current driver circuit in parallel with the current sensing resistor to reduce a gain in the circuit.

An ultrasound system driving architecture is also provided that is configured to drive an ultrasound transducer array with a plurality of ultrasound modalities, the ultrasound system driving architecture being configured to produce ultrasound pulses having microsecond-length and a peak negative pressure greater than 30 MPa for histotripsy therapies and being further configured to produce continuous wave ultrasound pulses having a peak negative pressure below 5 MPa for hyperthermia, hyperthermia/radio-sensitization, microbubble-enhanced drug delivery, blood brain barrier opening, immunotherapy, sonodynamic therapy, and neuromodulation therapies.

DETAILED DESCRIPTION

Provided herein are systems and methods that provide efficacious non-invasive and minimally invasive therapeutic, diagnostic and research procedures. In particular, provided herein are optimized systems and methods that provide targeted, efficacious ultrasound therapies in a variety of different regions and under a variety of different conditions without causing undesired tissue damage to intervening/non-target tissues or structures.

This disclosure further describes an All-In-One ultrasound (US) therapy system that can be used for a number of non-invasive ultrasound therapy modalities including Histotripsy. Hyperthermia/radio-sensitization, microbubble-enhanced drug delivery, immunotherapy, sonodynamic therapy, HIFU, and/or neuromodulation. This All-In-One US therapy system is capable of delivering different US modalities.

In some embodiments, the driving electronics described herein for an all-in-one ultrasound system includes transmit-receive driving electronics that are configured to deliver extremely high ultrasound pressure for histotripsy, ultrasound pulses for focal tissue thermal ablation (HIFU), lower pressure pulses at very high pulse repetition frequency (PRF) for hyperthermia, sonodynamic therapy, neuromodulation, and drug delivery, and receive the ultrasound signal for treatment monitoring and aberration correction. By changing the width of charge duration or the main power supply voltage, the output amplitude can be varied over large ranges for different therapeutic uses. In addition to short pulse histotripsy mode, the current driver is capable of quasi-CW operation by simply pulsing at very high rates and high duty cycle. The therapy transducer array elements can be used as receivers to detect cavitation emissions for treatment monitoring and/or aberration correction. The control system and receive data handling is performed by a set of FPGAs.

The system, methods and devices of the disclosure may be used for minimally or non-invasive acoustic cavitation and treatment of healthy, diseased and/or injured tissue, including in extracorporeal, percutaneous, endoscopic, laparoscopic, and/or as integrated into a robotically-enabled medical system and procedures. As will be described below, the histotripsy system may include various electrical, mechanical and software sub-systems, including a Cart, Therapy, Integrated Imaging, Robotics, Coupling and Software. The system also may comprise various Other Components, Ancillaries and Accessories, including but not limited to patient surfaces, tables or beds, computers, cables and connectors, networking devices, power supplies, displays, drawers/storage, doors, wheels, illumination and lighting and various simulation and training tools, etc. All systems, methods and means creating/controlling/delivering histotripsy are considered to be a part of this disclosure, including new related inventions disclosed herein.

In one embodiment, the ultrasound system is configured as a mobile therapy cart, which further includes a touchscreen display with an integrated control panel with a set of physical controls, a robotic arm, a therapy head positioned on the distal end of the robot, a patient coupling system and software to operate and control the system.

The mobile therapy cart architecture can comprise internal components, housed in a standard rack mount frame, including a histotripsy therapy generator, high voltage power supply, transformer, power distribution, robot controller, computer, router and modem, and an ultrasound imaging engine. The front system interface panel can comprise input/output locations for connectors, including those specifically for two ultrasound imaging probes (handheld and probe coaxially mounted in the therapy transducer), a histotripsy therapy transducer, AC power and circuit breaker switches, network connections and a foot pedal. The rear panel of the cart can comprise air inlet vents to direct airflow to air exhaust vents located in the side, top and bottom panels. The side panels of the cart include a holster and support mechanism for holding the handheld imaging probe. The base of the cart can be comprised of a cast base interfacing with the rack mounted electronics and providing an interface to the side panels and top cover. The base also includes four recessed casters with a single total locking mechanism. The top cover of the therapy cart can comprise the robot arm base and interface, and a circumferential handle that follows the contour of the cart body. The cart can have inner mounting features that allow technician access to cart components through access panels.

The touchscreen display and control panel may include user input features including physical controls in the form of six dials, a space mouse and touchpad, an indicator light bar, and an emergency stop, together configured to control imaging and therapy parameters, and the robot. The touchscreen support arm is configured to allow standing and seated positions, and adjustment of the touchscreen orientation and viewing angle. The support arm further can comprise a system level power button and USB and ethernet connectors.

The robotic arm can be mounted to the mobile therapy cart on arm base of sufficient height to allow reach and case of use positioning the arm in various drive modes into the patient/procedure work space from set up, through the procedure, and take down. The robotic arm can comprise six degrees of freedom with six rotating joints, a reach of 850 mm and a maximum payload of 5 kg. The arm may be controlled through the histotripsy system software as well as a 12 inch touchscreen polyscope with a graphical user interface. The robot can comprise force sensing and a tool flange, with force (x, y, z) with a range of 50 N, precision of 3.5 N and accuracy of 4.0 N, and torque (x, y, z) with a range of 10.0 Nm, precision of 0.2 Nm and accuracy of 0.3 Nm. The robot has a pose repeatability of +/−0.03 mm and a typical TCP speed of 1 m/s (39.4 in/s). In one embodiment, the robot control box has multiple I/O ports, including 16 digital in, 16 digital out, 2 analog in, 2 analog out and 4 quadrature digital inputs, and an I/O power supply of 24V/2 A. The control box communication comprises 500 Hz control frequency, Modbus TCP, PROFINET, ethernet/IP and USB 2.0 and 3.0.

The therapy head can comprise one of a select group of ultrasound therapy transducers and an ultrasound imaging system/probe, coaxially located in the therapy transducer, with an encoded mechanism to rotate said imaging probe independent of the therapy transducer to known positions, and a handle to allow gross and fine positioning of the therapy head, including user inputs for activating the robot (e.g. for free drive positioning). In some examples, the therapy transducers may vary in size (22×17 cm to 28×17 cm or 30 cm diameter hemispherical shaped), focal lengths from 12-18 cm, number of elements, ranging from 48 to 1000 elements, comprised within 12-16 rings, and with frequencies that support a plurality of ultrasound modalities (200 kHz-5 MHZ). The therapy head subsystem has an interface to the robotic arm includes a quick release mechanism to allow removing and/or changing the therapy head to allow cleaning, replacement and/or selection of an alternative therapy transducer design (e.g., of different number of elements and geometry), and each therapy transducer is electronically keyed for auto-identification in the system software.

The patient coupling system can comprise a six degree of freedom, six joint, mechanical arm, configured with a mounting bracket designed to interface to a surgical/interventional table rail. The arm may have a maximum reach of approximately 850 mm and an average diameter of 50 mm. The distal end of the arm can be configured to interface with an ultrasound medium container, including a frame system and an upper and lower boot. The lower boot is configured to support either a patient contacting film, sealed to patient, or an elastic polymer membrane, both designed to contain ultrasound medium (e.g., degassed water or water mixture), either within the frame and boot and in direct contact with the patient, or within the membrane/boot construct. The lower boot provides, in one example, a top and bottom window of approximately 46 cm×56 cm and 26 cm×20 cm, respectively, for placing the therapy transducer with the ultrasound medium container and localized on the patient's abdomen. The upper boot may be configured to allow the distal end of the robot to interface to the therapy head and/or transducer, and to prevent water leakage/spillage. In preferred embodiments, the upper boot is a sealed system. The frame is also configured, in a sealed system, to allow two-way fluid communication between the ultrasound medium container and an ultrasound medium source (e.g., reservoir or fluidics management system), including, but not limited for filling and draining, as well as air venting for bubble management.

The system software and work-flow can be configured to allow users to control the system through touchscreen display and the physical controls, including but not limited to, ultrasound imaging parameters and therapy parameters. The graphical user interface of the system comprises a work-flow based flow, with the general procedure steps of 1) registering/selecting a patient, 2) planning, comprising imaging the patient (and target location/anatomy) with the freehand imaging probe, and robot assisted imaging with the transducer head for final gross and fine targeting, including contouring the target with a target and margin contour, of which are typically spherical and ellipsoidal in nature, and running a test protocol (e.g., test pulses) including a bubble cloud calibration step, and a series of predetermined locations in the volume to assess cavitation initiation threshold and other patient/target specific parameters (e.g., treatment depth), that together inform a treatment plan accounting for said target's location and acoustic pathway, and any related blockage (e.g., tissue interfaces, bone, etc.) that may require varied levels of drive amplitude or frequency or phase/time delay to initiate and maintain the desired ultrasound modality. Said parameters, as measured as a part of a histotripsy test protocol, comprising calibration and multi-location test pulses, are configured in the system to provide input/feedback for updating bubble cloud location in space as needed/desired (e.g., appropriately calibrated to target cross-hairs), as well as determining/interpolating required amplitudes across all bubble cloud treatment locations in the treatment volume to ensure threshold is achieved throughout the volume. Further, said parameters, including but not limited to depth and drive voltage, may be also used as part of an embedded treatability matrix or look up table to determine if additional cooling is required (e.g., off-time in addition to time allocated to robot motions between treatment pattern movements) to ensure robust cavitation and intervening/collateral thermal effects are managed (e.g., staying below t43 curve for any known or calculated combination of sequence, pattern and pathway, and target depth/blockage). The work-flow and procedure steps associated with these facets of planning, as implemented in the system software may be automated, wherein the robot and controls system are configured to run through the test protocol and locations autonomously, or semi-autonomously. Following planning, the next phase of the procedure work-flow, 3) the treatment phase, is initiated following the user accepting the treatment plan and initiating the system for treatment. Following this command, the system is configured to deliver treatment autonomously, running the treatment protocol, until the prescribed volumetric treatment is complete. The status of the treatment (and location of the focal bubble cloud) is displayed in real-time, adjacent to various treatment parameters, including, but not limited to, of which may include total treatment time and remaining treatment time, drive voltage, treatment contours (target/margin) and bubble cloud/point locations, current location in treatment pattern (e.g., slice and column), imaging parameters, and other additional contextual data (e.g., optional DICOM data, force torque data from robot, etc.). Following treatment, the user may use the therapy head probe, and subsequently, the freehand ultrasound probe to review and verify treatment, as controlled/viewed through the system user interface. If additional target locations are desired, the user may plan/treat additional targets, or dock the robot to a home position on the cart if no further treatments are planned.

FIG. 1A generally illustrates an all-in-one ultrasound system 100 according to the present disclosure, comprising a therapy transducer 102, an imaging system 104, a display and control panel 106, a robotic positioning arm 108, and a cart 110. The cart can include circuitry including an electronic driver configured to drive the therapy transducer 102 to enable delivery of a plurality of ultrasound therapies or modalities, including Histotripsy, Hyperthermia/radio-sensitization, microbubble-enhanced drug delivery, immunotherapy, sonodynamic therapy, and/or neuromodulation. More specifically, the electronic drive can be configured to drive the single therapy transducer array to provide a plurality of ultrasound therapies. Previously, delivering multiple ultrasound therapies to a patient required separate therapy transducers for each patient and separate current drivers for each ultrasound modality. The electronic driver enables a plurality of ultrasound modalities with the same transducer array, from histotripsy requiring extremely high pressure and microsecond-length pulses at a very low duty to hyperthermia requiring ultrasound at low intensity and a very high duty cycle or continuous wave. The electronic driver also has transmit-and-receive capabilities to achieve aberration correction and cavitation detection during treatment. This allows the all-in-one ultrasound system described herein to be used outside a MRI scanner. The system can further include an ultrasound coupling interface and a source of coupling medium, not shown.

Table 1 is a listing of the various ultrasound modalities and typical parameters that the all-in-one ultrasound system is configured to support.

TABLE 1

| | US Modalities and Typical Parameters | |
|---|---|---|
| Modality | Use | Typical Ultrasound Parameters |
| Histotripsy | Ablation/ Immunostimulation | Pulse duration: μsec (1-2 cycle) P-: >15 MPa Duty cycle: <1% |
| HIFU/ Hyperthermia/ Radio-sensitization | Increase temperature to 40-45° C. for targeting on MRI; radio-sensitization; immunostimulation. | Continuous waves or long bursts with a high duty cycle Acoustic power: <500 W |
| Microbubble-enhanced drug delivery | Drug delivery (e.g., chemo drugs, tumor drugs, etc.) | Pulse duration: 10-100 msec P-: ~0.3-1.5 MPa Duty cycle: ~1-20% Microbubble injection |
| Immunotherapy | Leveraging the immuno-stimulation effect induced by histotripsy/ US thermal/US hyperthermia/US mechanical approaches | Histotripsy, hyperthermia, or Microbubble-enhanced drug delivery parameters |
| Sonodynamic therapy | US activation of sonosensitizers to drug delivery | Typically Continuous waves Intensity: 0.5-12 W/cm$^2$ Sonosensitizer |
| Neuromodulation | US modulates nerve functions for treatment of different neurological diseases | Pulse duration: msec to CW P-: 0.1-4 MPa Duty cycle: >0.1% |

FIG. 1B is a bottom view of the therapy transducer 102 and the imaging system 104. As shown, the imaging system can be positioned in the center of the therapy transducer. However, other embodiments can include the imaging system positioned in other locations within the therapy transducer, or even directly integrated into the therapy transducer. In some embodiments, the imaging system is configured to produce real-time imaging at a focal point of the therapy transducer. In some embodiments, a subset of the array elements can be configured to produce low pressure pulses, or pulses with a different frequency that other array elements.

The histotripsy system may comprise one or more of various sub-systems, including a Therapy sub-system that can create, apply, focus and deliver acoustic cavitation/ histotripsy through one or more therapy transducers, Integrated Imaging sub-system (or connectivity to) allowing real-time visualization of the treatment site and histotripsy effect through-out the procedure, a Robotics positioning sub-system to mechanically and/or electronically steer the therapy transducer, further enabled to connect/support or interact with a Coupling sub-system to allow acoustic coupling between the therapy transducer and the patient, and Software to communicate, control and interface with the system and computer-based control systems (and other external systems) and various Other Components, Ancillaries and Accessories, including one or more user interfaces and displays, and related guided work-flows, all working in part or together. The system may further comprise various fluidics and fluid management components, including but not limited to, pumps, valve and flow controls, temperature and degassing controls, and irrigation and aspiration capabilities, as well as providing and storing fluids. It may also contain various power supplies and protectors.

Cart

The Cart 110 may be generally configured in a variety of ways and form factors based on the specific uses and procedures. In some cases, systems may comprise multiple Carts, configured with similar or different arrangements. In some embodiments, the cart may be configured and arranged to be used in a radiology environment and in some cases in concert with imaging (e.g., CT, cone beam CT and/or MRI scanning). In other embodiments, it may be arranged for use in an operating room and a sterile environment, or in a robotically enabled operating room, and used alone, or as part of a surgical robotics procedure wherein a surgical robot conducts specific tasks before, during or after use of the system and delivery of acoustic cavitation/histotripsy. As such and depending on the procedure environment based on the aforementioned embodiments, the cart may be positioned to provide sufficient work-space and access to various anatomical locations on the patient (e.g., torso, abdomen, flank, head and neck, etc.), as well as providing work-space for other systems (e.g., anesthesia cart, laparoscopic tower, surgical robot, endoscope tower, etc.).

The Cart may also work with a patient surface (e.g., table or bed) to allow the patient to be presented and repositioned in a plethora of positions, angles and orientations, including allowing changes to such to be made pre, peri and post-procedurally. It may further comprise the ability to interface and communicate with one or more external imaging or image data management and communication systems, not limited to ultrasound, CT, fluoroscopy, cone beam CT, PET, PET/CT, MRI, optical, ultrasound, and image fusion and or image flow, of one or more modalities, to support the procedures and/or environments of use, including physical/ mechanical interoperability (e.g., compatible within cone beam CT work-space for collecting imaging data pre-, peri- and/or post-histotripsy).

In some embodiments one or more Carts may be configured to work together. As an example, one Cart may comprise a bedside mobile Cart equipped with one or more Robotic arms enabled with a Therapy transducer, and Therapy generator/amplifier, etc., while a companion cart working in concert and at a distance of the patient may comprise Integrated Imaging and a console/display for controlling the Robotic and Therapy facets, analogous to a surgical robot and master/slave configurations.

In some embodiments, the system may comprise a plurality of Carts, all slave to one master Cart, equipped to conduct acoustic cavitation procedures. In some arrangements and cases, one Cart configuration may allow for storage of specific sub-systems at a distance reducing operating room clutter, while another in concert Cart may comprise essentially bedside sub-systems and componentry (e.g., delivery system and therapy).

One can envision a plethora of permutations and configurations of Cart design, and these examples are in no way limiting the scope of the disclosure.

Histotripsy

Histotripsy comprises short, high amplitude, focused ultrasound pulses to generate a dense, energetic, "bubble cloud", capable of the targeted fractionation and destruction of tissue. Histotripsy is capable of creating controlled tissue erosion when directed at a tissue interface, including tissue/ fluid interfaces, as well as well-demarcated tissue fractionation and destruction, at sub-cellular levels, when it is targeted at bulk tissue. Unlike other forms of ablation, including thermal and radiation-based modalities, histotripsy does not rely on heat or ionizing (high) energy to treat tissue. Instead, histotripsy uses acoustic cavitation generated at the focus to mechanically effect tissue structure, and in some cases liquefy, suspend, solubilize and/or disrupt tissue into sub-cellular components.

Histotripsy can be applied in various forms, including: 1) Intrinsic-Threshold Histotripsy: Delivers pulses with at least a single negative/tensile phase sufficient to cause a cluster of bubble nuclei intrinsic to the medium to undergo inertial cavitation, 2) Shock-Scattering Histotripsy: Delivers typically pulses 3-20 cycles in duration. The amplitude of the tensile phases of the pulses is sufficient to cause bubble nuclei in the medium to undergo inertial cavitation within the focal zone throughout the duration of the pulse. These nuclei scatter the incident shockwaves, which invert and constructively interfere with the incident wave to exceed the threshold for intrinsic nucleation, and 3) Boiling Histotripsy: Employs pulses roughly 1-20 ms in duration. Absorption of the shocked pulse rapidly heats the medium, thereby reducing the threshold for intrinsic nuclei. Once this intrinsic threshold coincides with the peak negative pressure of the incident wave, boiling bubbles form at the focus. Alternatively, the 1-20 ms pulse can reach boiling temperature to form boiling bubbles.

The large pressure generated at the focus causes a cloud of acoustic cavitation bubbles to form above certain thresholds, which creates localized stress and strain in the tissue and mechanical breakdown without significant heat deposition. At pressure levels where cavitation is not generated, minimal effect is observed on the tissue at the focus. This cavitation effect is observed only at pressure levels significantly greater than those which define the inertial cavitation threshold in water for similar pulse durations, on the order of 10 to 30 MPa peak negative pressure.

Histotripsy may be performed in multiple ways and under different parameters. It may be performed totally non-invasively by acoustically coupling a focused ultrasound transducer over the skin of a patient and transmitting acoustic pulses transcutaneously through overlying (and intervening) tissue to the focal zone (treatment zone and site). It may be further targeted, planned, directed and observed under direct visualization, via ultrasound imaging, given the bubble clouds generated by histotripsy may be visible as highly dynamic, echogenic regions on, for example, B Mode ultrasound images, allowing continuous visualization through its use (and related procedures). Likewise, the treated and fractionated tissue shows a dynamic change in echogenicity (typically a reduction), which can be used to evaluate, plan, observe and monitor treatment.

Generally, in histotripsy treatments, ultrasound pulses with 3 or more acoustic cycles are applied, and the bubble cloud formation relies on the pressure release scattering of the positive shock fronts (sometimes exceeding 100 MPa, P+) from initially initiated, sparsely distributed bubbles (or a single bubble). This is referred to as the "shock scattering mechanism".

This mechanism depends on one (or a few sparsely distributed) bubble(s) initiated with the initial negative half cycle(s) of the pulse at the focus of the transducer. A cloud of microbubbles then forms due to the pressure release backscattering of the high peak positive shock fronts from these sparsely initiated bubbles. These back-scattered high-amplitude rarefactional waves exceed the intrinsic threshold thus producing a localized dense bubble cloud. Each of the following acoustic cycles then induces further cavitation by the backscattering from the bubble cloud surface, which grows towards the transducer. As a result, an elongated dense bubble cloud growing along the acoustic axis opposite the ultrasound propagation direction is observed with the shock scattering mechanism. This shock scattering process makes the bubble cloud generation not only dependent on the peak negative pressure, but also the number of acoustic cycles and the amplitudes of the positive shocks. Without at least one intense shock front developed by nonlinear propagation, no dense bubble clouds are generated when the peak negative half-cycles are below the intrinsic threshold.

When ultrasound pulses less than 2 cycles are applied, shock scattering can be minimized, and the generation of a dense bubble cloud depends on the negative half cycle(s) of the applied ultrasound pulses exceeding an "intrinsic threshold" of the medium. This is referred to as the "intrinsic threshold mechanism".

This threshold can be in the range of 26-30 MPa for soft tissues with high water content, such as tissues in the human body. In some embodiments, using this intrinsic threshold mechanism, the spatial extent of the lesion may be well-defined and more predictable. With peak negative pressures (P−) not significantly higher than this threshold, sub-wavelength reproducible lesions as small as half of the −6 dB beam width of a transducer may be generated.

With high-frequency Histotripsy pulses, the size of the smallest reproducible lesion becomes smaller, which is beneficial in applications that require precise lesion generation. However, high-frequency pulses are more susceptible to attenuation and aberration, rendering problematical treatments at a larger penetration depth (e.g., ablation deep in the body) or through a highly aberrative medium (e.g., transcranial procedures, or procedures in which the pulses are transmitted through bone(s)). Histotripsy may further also be applied as a low-frequency "pump" pulse (typically <2 cycles and having a frequency between 100 kHz and 1 MHZ) can be applied together with a high-frequency "probe" pulse (typically <2 cycles and having a frequency greater than 2 MHZ, or ranging between 2 MHz and 10 MHZ) wherein the peak negative pressures of the low and high-frequency pulses constructively interfere to exceed the intrinsic threshold in the target tissue or medium. The low-frequency pulse, which is more resistant to attenuation and aberration, can raise the peak negative pressure P− level for a region of interest (ROI), while the high-frequency pulse, which provides more precision, can pinpoint a targeted location within the ROI and raise the peak negative pressure P− above the intrinsic threshold. This approach may be referred to as "dual frequency", "dual beam histotripsy" or "parametric histotripsy."

Additional systems, methods and parameters to deliver optimized histotripsy, using shock scattering, intrinsic threshold, and various parameters enabling frequency compounding and bubble manipulation, are herein included as part of the system and methods disclosed herein, including additional means of controlling said histotripsy effect as pertains to steering and positioning the focus, and concurrently managing tissue effects (e.g., prefocal thermal collateral damage) at the treatment site or within intervening tissue. Further, it is disclosed that the various systems and methods, which may include a plurality of parameters, such as but not limited to, frequency, operating frequency, center frequency, pulse repetition frequency, pulses, bursts, number of pulses, cycles, length of pulses, amplitude of pulses, pulse period, delays, burst repetition frequency, sets of the former, loops of multiple sets, loops of multiple and/or different sets, sets of loops, and various combinations or permutations of, etc., are included as a part of this disclosure, including future envisioned embodiments of such.

Technical Challenges with Histotripsy

There are two technical challenges for using ultrasound therapy such as histotripsy to treat a deep tissue target (e.g., >8 cm) or through heterogenous tissue: 1) acoustic aberration and 2) real-time feedback of the ultrasound therapy.

Acoustic aberration is a problem that impacts ultrasound therapy and imaging, including histotripsy. Acoustic aberration can reduce the focal pressure and distort the focus due to ultrasound propagation through multi-layer heterogenous tissue. Reduction of the focal pressure can cause ineffective treatment or reduced treatment efficiency. For example, in histotripsy, focal pressures at the target tissue site are precisely controlled to generate cavitation at the target tissue site. Reduction of the focal pressures due to aberration can prevent cavitation from occurring. Distortion of the focus can also decrease treatment accuracy. Typically, a focused ultrasound transducer is shaped as a segment of a spherical surface, such that the sound wave emitted from all locations from the transducer surface go through the same distance to arrive at the focus at the same time. However, due to the variation of speed of sound across bones and heterogeneous soft tissue, the travel time from different elements of an ultrasound transducer array to arrive at the focus may be different. As a result, aberration can result in loss of focal pressure and defocusing, decreasing treatment efficacy and accuracy.

As ultrasound is a non-invasive therapy technique, real-time feedback is critical to achieve high treatment accuracy and minimizing any potential complications. Ultrasound imaging has been used to provide real-time feedback for histotripsy, as histotripsy-generated cavitation can be visualized on ultrasound images as a dynamic, bright zone. Typically, an ultrasound imaging probe is inserted in a central hole of the histotripsy transducer, thus the 2D ultrasound imaging plane contains the histotripsy focus. Ultrasound imaging can then be used to guide the targeting to place histotripsy focus to the correct target tissue and to monitor the treatment progression. However, there are two main limitations of using ultrasound imaging as the sole guidance for histotripsy. 1) When the ultrasound imaging probe is blocked by bone of the patient (e.g., ribs or skull), ultrasound images of the histotripsy focus cannot be obtained. For example, histotripsy can be used to treat a tumor volume in the liver of a patient, which is partially behind the ribcage. When the histotripsy transducer is mechanically moved to scan the histotripsy focus to cover the tumor volume, the imaging probe can be blocked by the ribs for a certain duration of the therapy, at which point no real-time imaging of the therapy is available due to the rib blockage. Without any feedback during this duration, there is no way of knowing if cavitation is still generated at the target locations in the tumor (i.e., if the treatment is implemented over this duration). 2) Ultrasound imaging probes can only view the tissue and cavitation within the 2D image plane that contains the histotripsy focus. Thus, ultrasound imaging probes cannot view any potential unwanted cavitation occurring outside the image plane. Unwanted cavitation may generate undesired off-target damage.

The problems described above can be solved with a novel histotripsy ultrasound phased array transducer, as described herein, that is configured to transmit ultrasound signals to generate cavitation and deliver histotripsy as well as is configured to receive ultrasound signals (i.e., a transmit-receive histotripsy array).

For example, when the ultrasound therapy transducer comprises a phased array, phase correction techniques can be used to correct aberration to recover reduced focal pressure. This can be accomplished by adjusting the phase/time delay at transmission from each transducer element of the phased array to compensate for the travel time variation from each array element to the focus due to the speed of sound variation. In doing so, the aberration can be corrected to increase the focal pressure and improve the focusing.

An ultrasound phased array transducer that can delivery histotripsy and receive acoustic cavitation emission signals can further be configured to allow detection, localization, and mapping of cavitation. Currently, a typical histotripsy system only transmits ultrasound pulses to generate cavitation at the focus. A transmit-receive histotripsy system can not only be used to deliver ultrasound pulses to generate cavitation, but also can receive signals such as the acoustic cavitation emission (ACE) signals. Both the rapid expansion and rapid collapse of cavitating bubbles during histotripsy produce shockwaves that can be detected by an acoustic receiver. In some embodiments, received reflections of the main therapy pulse (if >1-2 cycles long and not fully transformed to shockwave in cavitation generation event) or subsequent low amplitude therapy pulses could be used in various receive application listed below. By processing the ACE signals received from a histotripsy transducer array system with hundreds of elements and transmit-receive capability, cavitation can be detected and localized to provide a real-time, 3D cavitation map. The acoustic emission signals from the growth and/or collapse of histotripsy-induced cavitation microbubbles, received by the histotripsy array, can be used to localize and monitor the cavitation in 3D and real-time, even in situations where the ultrasound imaging probe is blocked by bone. 3D cavitation mapping can also allow real-time monitoring of any off-focus cavitation to increase safety and identify unwanted cavitation.

Transmit-receive driving electronics found in typical phased array systems cannot be directly adapted for a histotripsy phased array transducer because of the extremely high voltages (thousands of volts) necessary for generating high-pressure histotripsy pulses. A novel driving electronics, as described herein, is configured to safely block or significantly attenuate the transmit signal to the ultrasound transducer array while maintaining high sensitivity and high dynamic range for received ultrasound signals. This disclosure provides both hardware and software for a phased array histotripsy transducer array with transmit and receive capability. This disclosure further describes the methods and signal processing algorithms that can be used with the transmit-receive histotripsy system for aberration correction and cavitation mapping.

Electronic Driver Transmit Architecture

FIG. 2A shows a simplified schematic of an electronic driver 200 with the key components for ultrasound transmission. This design is a type of "current driver" system producing very short half cycle drive pulses. A digital drive signal 202 (chan_drive) coming from a controller FPGA provides an input to an isolated transistor gate driver 204 (such as SI8261AAC). For histotripsy use, the gate signal can pulse the transistor Q1 at a pulse repetition frequency (PRF) ranging from 1 Hz to 1 kHz with a gate signal pulse width for typically set between 1 usec and 5 usec. This can cause the transistor to turn on for a brief period (~1-5 usec) pulling current through the primary of the transformer T1. Q1 then turns off forcing the built up current out to secondary side of T1 to the therapy transducer of the all-in-one ultrasound system. Varying the duration of the transistor on-time adjusts the output linearly as the current will increase linearly in the transformer assuming ideal components (dI/dt=power supply/Inductance). The inductance of the secondary winding is chosen to resonate with the capacitance of the therapy transducer such that a damped sinusoidal output would be produced at the transducer operating frequency. Optional blocking diode D1 (e.g., 1200 V rated silicon carbide material) prevents the transistor Q1 from conducting when the polarity goes negative. Removing D1 from the schematic provides shorter pulses and a lower power output. Later cycles are significantly attenuated by the electrical and mechanical loss in the transducer as well as the radiated sound giving a very short output response. Components R1 and C1 combine to slow down the turn-on and turn-off of the transistor Q1 to reduce RF noise emissions. There is a tradeoff between power efficiency and electrical noise that can be optimized with component selection. For example, if the transistor is switched off too rapidly, high frequency cable resonances can be excited which don't contribute to useful acoustic output. Typically, Q1 is a silicon carbide based transistor (such as UF3C120150B7S) capable of switching at high speed for high power efficiency. C1 also helps prevent an arc fault on the output or other failures from causing Q1 to turn on inappropriately due to feedback through the Miller capacitance. Alternatively, a transistor gate driver other than the SI8261AAC such as the 1ED3122MC12H could be used which has an integrated Miller clamp circuit to accomplish the same function.

For histotripsy use, the current driver system has a driver transformer T1. Use of a transformer allows a step up turns ratio (1:N turns ratio) such that the transistor Q1 is not required to have as high a breakdown voltage. Suitable transistors with a rating of 1200 V or less are readily available while higher voltage rating parts are very rare. Typical ultrasound therapy transducers may require as much as 3000 V or more to perform histotripsy. Type 3 or type 14 iron powder toroid cores work extremely well for this purpose. The inductance of the secondary winding (attached to transducer) determines the drive frequency.

Capacitor C2 stores energy for the high peak power output during a histotripsy pulse. Resistor R2 isolates different channels within a phased array system to minimize cross talk and to ensure a consistent output when only a single channel is pulsed versus the full array. This resistor also limits the peak energy available to the amount stored in C2 in case of a component failure or other circuit fault on the channel. A phased array system with hundreds of channels would be at risk of an electrical fire in case of a circuit fault from the large amount of stored energy in the capacitors C2 associated with each channel. An alternate strategy to reduce this risk is to use a fuse in place of resistor R2. 100 V is usually adequate for the main power supply (channel drive voltage) while still generating pulses up to several thousand volts on the output which is the principal advantage of the current driver circuit.

For the ultrasound modes other than histotripsy, when lower pressure ultrasound at a high PRF or continuous wave (CW) is used, quasi-CW operation is possible with this driving electronics design by setting very high PRFs for the channel drive signal at lower amplitude. For example, the gate signal can be pulsed at 1 MHz pulse repetition rate (PRF) with 500 ns wide pulses to generate a 1 MHz tone burst output. Optimization for this quasi-CW mode generally needs different components than optimization for histotripsy, but a compromise system may be sufficient for both. Changes include selecting gate drive components for higher efficiency and selection of the main transistor Q1. A circuit board layout designed for forced air cooling should greatly increase output capability. Higher current power supplies could also be required. The embodiment shown here is capable of running continuously at 1 MHz and 5 W/channel output electrical power without forced air cooling. In histotripsy mode, greater than 3 kV and 20 A/channel is possible with the same circuit.

FIG. 2B is a power supply switching circuit configured to provide power for a plurality of operation modes, such as histotripsy, HIFU, etc. This power supply switching circuit feeds the current driver circuits shown on FIG. 2A allowing relatively rapid switching between operation modes. Turning on transistor Q1 connects the drivers to a lower voltage (+48), high current power supply and system bypass capacitor C1 for operating in CW modes. Turning on transistor Q2 instead connects the driver to a higher voltage (+100), but lower current power supply suitable for histotripsy mode. This dual supply configuration has the potential to greatly reduce the cost of the system compared to a single supply which would need to be capable of providing high voltage, high current, and adjustability. Additionally, this may allow operation of the system with only single phase 120 VAC and not requiring 220 VAC. Not shown on the simplified schematic of FIG. 2B are standard gate drive components associated with the "high side" switch configurations for Q1 and Q2. These could be SI8261AAC isolated gate drivers, for example.

Electronic Driver Receive Architecture

In order to use the same transducer array for transmit and receive, the digitizer must be capable of rejecting large transmit voltages and currents. A traditional transmit/receive ultrasound switch is not practical because of the very large drive voltages for histotripsy therapy. One alternative is to attenuate the signals with a capacitive divider (as used by oscilloscope probes). The disadvantage of this method is that the sensitivity becomes very low and a very large dynamic range is required. Signal-to-noise-ratio (SNR) for weak receive signals is particularly low. A limiting circuit can be used to improve resolution for small signals or a nonlinear gain curve, but neither can achieve the same SNR as a transmit/receive switch or receive only channel.

Another alternative is a "current receive" electronic driver 300 shown in FIG. 3. The current receive electronic driver of FIG. 3 is configured to drive transmission of ultrasound pulses through the ultrasound therapy transducer array, and is also configured to enable sensing or receive functionality of ultrasound signals with the ultrasound therapy transducer array. A current sensing resistor R1 is placed in the ground side return path from the output transformer T1. A digitizer 302 such as AFE5801 can measure the voltage across this resistor. Because ultrasound transducers are a capacitive load and the bandwidth is relatively narrow, the current is very similar to the voltage with merely a phase shift. Ultrasound imaging transducers have very small elements that produce extremely small charge/current as receivers so this would be impractical for a typical imager. Ultrasound therapy elements, on the other hand, have thousands of times larger surface area than imaging transducers, so they can produce large currents. On transmission, peak current can be 20 A or greater while desired receive signals can be as small as a fraction of a mA.

Transmit currents can be blocked with a pair of bypass diodes in parallel with the sensing resistor R1. This is standard practice for current measuring devices. In the embodiment of FIG. 3, however, the driver 300 uses a pair of low threshold MOSFETs (CSD16301Q2, for example) for this function (Q1, Q2). They provide a larger sense range (in the "off" state) that better matches the input to the ADC, and a higher "on" state conductivity and switching speed all in a smaller package than any diodes. A gate driver using a bipolar power supply such as the SI8261AAC shown can force these transistors fully on or off depending on transmit/receive state for optimal performance.

To further extend the dynamic range for the current receive system, the driver 300 includes two sets of sense resistors. The default higher sensitivity setting is a large resistance (e.g., 200 ohm) resistor R1. Turning on a pair of small signal MOSFETs (Q3, Q4) switches in a smaller resistance (e.g., 5 ohm) sense resistor R2 in parallel, which reduces the gain (e.g., by approximately 32 dB with the resistances described above). This is in addition to the variable gain amplifier within the digitizer. The large resistor R1 is still a relatively low impedance so there is no change in SNR between the two ranges. A single control line could set the current range for all channels or this could potentially be on a per channel basis. This setting can be changed and the output stabilized in less than a few microseconds so the current range can be changed in the middle of a receive acquisition to reduce strong reflections or amplify portions of the trace. The digitizer can be designed for a balanced input using an RF signal transformer T2 for the best SNR and dynamic range. The transformer allows electrical isolation to be maintained between the driver output and digital electronics, but is not capable of any high voltage isolation protection. R3 limits the current of any residual transient over-voltages from the bypass circuit to prevent harm to the ADC. C1 and C2 are specified for the digitizer as the input is meant to be capacitively coupled. All the power supplies interfacing to the receive section should be low noise to achieve the best SNR (the +/−9V supply for the gain switch and the digitizer).

MRI Compatibility and Imaging

Other than the electronic driver, all components of the all-in-one ultrasound system are MRI compatible. Long cables can be used to connect the ultrasound array and the electronic driver, such that the ultrasound array can be placed inside an MRI scanner, and the electronic driver can be placed outside the scanner room in the control room. As such, this all-in-one ultrasound system can be used with MRI to guide and monitor the treatment.

Targeting

The all-in-one system can be guided by ultrasound imaging. MRI, or surgical navigation system.

When using MR guidance, MR thermometry and low heating can be used for targeting. For targeting, the all-in-one ultrasound system can function at the hyperthermia mode to increase the temperature in the US focal zone by 1-2° C. The MR thermometry can be used to identify and mark the focal location on the MR image.

Aberration Correction

Aberration correction can be necessary for brain treatment, due to the aberration induced by ultrasound propagation through the skull with varying thickness and different speed of sound from soft tissue. The ultrasound array can include fiducial markers that can be imaged on MRI. The MR images containing the patient's head and the ultrasound array can then be co-registered with pre-treatment imaging (e.g., CT scan of the patient head) by aligning the skull. The ultrasound array location with regard to the skull can be identified based on the MR fiducial markers on the array. Aberration correction can be performed using a ray-tracing approach based on the skull location, thickness, speed of sound, and relative location to the ultrasound array. It is also possible to use MR images to measure the skull thickness for aberration correction, without requiring pre-treatment CT head scan.

Monitoring

To monitor temperature increases in the tissue, MR thermometry can be used. To monitor cavitation, diffusionweighted MRI can be synchronized with the ultrasound delivery to image the local movement induced by cavitation.

When using surgical navigation system to guide the treatment, the ultrasound array has transmit-and-receive capabilities, such that the cavitation emission signals can be received by each of the array element and processed to detect and map the cavitation during treatment using the computer that controls the ultrasound array. The cavitation map can be overlaid on the pre-treatment 3D MR image on the surgical navigation system of the target tissue.

When using ultrasound imaging to guide the treatment, cavitation can be directly visualized on real-time ultrasound images.

Methods of Use

Many novel and inventive therapy methods can be implemented with the all-in-one ultrasound system described herein. Prior to this disclosure, delivery of a plurality of different ultrasound therapies and/or modalities was not possible with a single ultrasound system. The novel electronic driver and transducer arrays described herein enable this new functionality.

Referring to FIG. 4, a flowchart is illustrated that includes applying a plurality of different ultrasound modalities to treat a target tissue. For example, referring to step 402 of the flowchart of FIG. 4, a target tissue can be identified. The target tissue can comprise, for example, a liver, a brain, a tumor, a prostate, etc. In some embodiments, the target tissue can be identified with real-time imaging, which can be integrated within an all-in-one ultrasound system or separate from the system.

At step 404, the method can comprise applying a first or primary ultrasound therapy modality, such as histotripsy therapy, to the target tissue with a current driver and a therapy transducer array of the all-in-one ultrasound system. As described above, the electronics driver of the all-in-one system can be configured to deliver a plurality of user-selectable ultrasound modalities to a target tissue with a single or the same ultrasound therapy transducer array. The modalities can include, in addition to histotripsy, HIFU, Hyperthermia/radio-sensitization, microbubble-enhanced drug delivery, immunotherapy, sonodynamic therapy, and/or neuromodulation. While method step 404 is described and illustrated as providing histotripsy as the primary ultrasound therapy modality, it is merely optional that the primary ultrasound modality provided by the all-in-one system be histotripsy. In other embodiments, the primary ultrasound therapy modality can comprise any other ultrasound modality supported by the current driver, including, for example, HIFU, Hyperthermia/radio-sensitization, microbubble-enhanced drug delivery, immunotherapy, sonodynamic therapy, and/or neuromodulation.

Next, at step 406, the method can include selecting a second or different ultrasound modality in the all-in-one ultrasound system. As described above, if the first or primary ultrasound therapy modality comprises histotripsy, the second or different ultrasound modality can include Hyperthermia/radio-sensitization, microbubble-enhanced drug delivery, immunotherapy, sonodynamic therapy, and/or neuromodulation. In embodiments where the first ultrasound therapy modality is not histotripsy, then the second or different ultrasound therapy modality can comprise histotripsy.

Finally, at step 408, the method can comprise applying the different ultrasound modality to the target tissue with the current driver and the ultrasound therapy transducer array of the all-in-one ultrasound system.

For example, histotripsy can be used with drug delivery or sonodynamic therapy, such that histotripsy is used debulk the core tumor, while ultrasound drug delivery or sonodynamic therapy is used at the tumor periphery to treat the diffused tumor cells. Histotripsy or ultrasound drug delivery can also be combined with ultrasound immunotherapy, such that histotripsy or ultrasound drug delivery is used to treat the local tumor, while ultrasound immunotherapy is used to treat distant tumors.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. An ultrasound system driving architecture configured to drive an ultrasound transducer array with a plurality of ultrasound modalities, the ultrasound system driving architecture comprising:

a power supply switching circuit configured to switch between a first power mode that provides a first voltage and a first current and a second power mode that provides a second voltage and a second current, wherein the second voltage is higher than the first voltage and the second current is lower than the first current; and a current driver circuit comprising a gate driver configured to receive a digital drive signal, a transformer electrically coupled to the ultrasound transducer array, a transistor electrically coupled to the gate driver and the transformer, and a first resistor and a first capacitor electrically coupled to the transistor and configured to slow down a turn-on time and a turn-off time of the transistor to reduce RF noise emissions, wherein the gate driver is configured to drive the transistor at a first pulse repetition frequency when the power supply switching circuit is operating in the first power mode to produce ultrasound pulses of a first ultrasound therapy modality, and wherein the gate driver is configured to drive the transistor at a second pulse repetition frequency when the power supply switching circuit is operating in the second power mode to produce ultrasound pulses of a second ultrasound therapy modality.

2. The ultrasound driving system architecture of claim 1, wherein the first ultrasound therapy modality is selected from the group consisting of hyperthermia/radio-sensitization, HIFU, microbubble-enhanced drug delivery, immunotherapy, sonodynamic therapy, and neuromodulation.

3. The ultrasound driving system architecture of claim 1, wherein the second ultrasound therapy modality comprises histotripsy.

4. The ultrasound driving system architecture of claim 1, further comprising a blocking diode electrically connected to the transistor and configured to prevent the transistor from conducting when a polarity of the transistor is negative.

5. The ultrasound driving system architecture of claim 1, wherein a secondary winding of the transformer is configured to resonate with a capacitance of the ultrasound transducer array.

6. The ultrasound driving system architecture of claim 1, wherein the power supply switching circuit further comprises:

a first transistor configured to connect the power supply switching circuit to a first power supply; and a second transistor configured to connect the power supply switching circuit to a second power supply.

7. The ultrasound driving system architecture of claim 1, wherein the current driver circuit is further configured to enable the ultrasound transducer array to measure ultrasound signals.

8. The ultrasound driving system architecture of claim 7, wherein the current driver circuit further comprises a current sensing resistor and a digitizer configured to measure a voltage across the current sensing resistor.

9. The ultrasound driving system architecture of claim 8, further comprising a pair of MOSFETs in parallel with the current sensing resistor configured to block transmit currents.

10. The ultrasound driving system architecture of claim 8, further comprising a second current sensing resistor configured to be switched into the current driver circuit in parallel with the current sensing resistor to reduce a gain in the circuit.

11. An ultrasound system driving architecture configured to drive an ultrasound transducer array with a plurality of ultrasound modalities, the ultrasound system driving architecture comprising:

a power supply switching circuit configured to switch between a first power mode that provides a first voltage and a first current and a second power mode that provides a second voltage and a second current, wherein the second voltage is higher than the first voltage and the second current is lower than the first current; and a current driver circuit comprising a gate driver configured to receive a digital drive signal, a transformer electrically coupled to the ultrasound transducer array, a transistor electrically coupled to the gate driver and the transformer, and a blocking diode electrically connected to the transistor and configured to prevent the transistor from conducting when a polarity of the transistor is negative, wherein the gate driver is configured to drive the transistor at a first pulse repetition frequency when the power supply switching circuit is operating in the first power mode to produce ultrasound pulses of a first ultrasound therapy modality, and wherein the gate driver is configured to drive the transistor at a second pulse repetition frequency when the power supply switching circuit is operating in the second power mode to produce ultrasound pulses of a second ultrasound therapy modality.

12. The ultrasound driving system architecture of claim 11, wherein the first ultrasound therapy modality is selected from the group consisting of hyperthermia/radio-sensitization, HIFU, microbubble-enhanced drug delivery, immunotherapy, sonodynamic therapy, and neuromodulation.

13. The ultrasound driving system architecture of claim 11, wherein the second ultrasound therapy modality comprises histotripsy.

14. The ultrasound driving system architecture of claim 11, wherein a secondary winding of the transformer is configured to resonate with a capacitance of the ultrasound transducer array.

15. The ultrasound driving system architecture of claim 11, wherein the power supply switching circuit further comprises:

a first transistor configured to connect the power supply switching circuit to a first power supply; and a second transistor configured to connect the power supply switching circuit to a second power supply.

16. The ultrasound driving system architecture of claim 11, wherein the current driver circuit is further configured to enable the ultrasound transducer array to measure ultrasound signals.

17. The ultrasound driving system architecture of claim 16, wherein the current driver circuit further comprises a current sensing resistor and a digitizer configured to measure a voltage across the current sensing resistor.

18. The ultrasound driving system architecture of claim 17, further comprising a pair of MOSFETs in parallel with the current sensing resistor configured to block transmit currents.

19. The ultrasound driving system architecture of claim 17, further comprising a second current sensing resistor configured to be switched into the current driver circuit in parallel with the current sensing resistor to reduce a gain in the circuit.

* * * * *